(12) United States Patent
Fried et al.

(10) Patent No.: US 10,827,925 B2
(45) Date of Patent: Nov. 10, 2020

(54) REMOTE COMPREHENSIVE EYE EXAMINATION SYSTEM

(71) Applicant: DigitalOptometrics LLC, Lake Success, NY (US)

(72) Inventors: Howard S. Fried, Roslyn, NY (US); Burton T. Fried, Westport, CT (US); Kurt Schaeffer, Waynesboro, VA (US); William K. Van Cleave, Abilene, TX (US)

(73) Assignee: DigitalOptometrics LLC, Lake Success, NY (US)

( * ) Notice: Subject to any disclaimer, the term of this patent is extended or adjusted under 35 U.S.C. 154(b) by 214 days.

(21) Appl. No.: 16/138,081

(22) Filed: Sep. 21, 2018

(65) Prior Publication Data
US 2019/0029516 A1   Jan. 31, 2019

Related U.S. Application Data

(63) Continuation-in-part of application No. 15/916,639, filed on Mar. 9, 2018, now Pat. No. 10,524,658, (Continued)

(51) Int. Cl.
*A61B 3/18* (2006.01)
*G16H 40/67* (2018.01)
(Continued)

(52) U.S. Cl.
CPC .............. *A61B 3/18* (2013.01); *A61B 3/0285* (2013.01); *A61B 3/14* (2013.01); *G16H 20/30* (2018.01);
(Continued)

(58) Field of Classification Search
CPC ........ A61B 3/18; A61B 3/0285; G16H 40/67; G16H 80/00; G16H 10/60; G16H 50/20
See application file for complete search history.

(56) References Cited

U.S. PATENT DOCUMENTS 5,914,772 A   6/1999  Dyer
5,956,121 A   9/1999  Hosoi
(Continued)

FOREIGN PATENT DOCUMENTS

CN   102727175 A   10/2012
WO     9617545 A1    6/1996
(Continued)

OTHER PUBLICATIONS

American Optometrics Association, Position Statement Regarding Eye and Vision Telehealth Services (Approved Feb. 2017).
(Continued)

*Primary Examiner* — Jack Dinh
(74) *Attorney, Agent, or Firm* — Fish & Richardson P.C.

(57) ABSTRACT

An ophthalmic technician is present with a patient in an exam room to operate eye examination equipment and transmit patient information to remote location. At that remote location, a skilled technician is present to provide the necessary optical care, and may operate the phoropter from the remote location. Using video and/or teleconferencing equipment and a phoropter located in the patient examination room along with management software, the system works to determine the final optical prescription for the patient. That information, coupled with findings from other devices which are integrated with the management software, and that the patient uses locally, are reviewed by a remote-based optometrist or ophthalmologist.

20 Claims, 18 Drawing Sheets

Related U.S. Application Data which is a continuation of application No. 15/699,533, filed on Sep. 8, 2017, now Pat. No. 9,980,644.

(60) Provisional application No. 62/394,369, filed on Sep. 14, 2016.

(51) Int. Cl.

| | | |
|---|---|---|
| *A61B 3/028* | (2006.01) | |
| *G16H 10/60* | (2018.01) | |
| *G16H 50/20* | (2018.01) | |
| *A61B 3/14* | (2006.01) | |
| *G16H 80/00* | (2018.01) | |
| *G16H 20/30* | (2018.01) | |

(52) U.S. Cl.
CPC ............. *G16H 40/67* (2018.01); *G16H 50/20* (2018.01); *G16H 80/00* (2018.01); *G16H 10/60* (2018.01)

(56) References Cited

U.S. PATENT DOCUMENTS

| | | |
|---|---|---|
| 6,499,843 B1 | 12/2002 | Cox et al. |
| 7,232,220 B2 | 6/2007 | Franz et al. |
| 7,520,611 B2 | 4/2009 | Franz et al. |
| 7,818,041 B2 | 10/2010 | Kim |
| 7,840,418 B2 | 11/2010 | Schoenberg |
| 8,444,270 B2 | 5/2013 | Nordstrom |
| 8,793,142 B2 | 7/2014 | Fishman |
| 9,230,062 B2 | 1/2016 | Seriani |
| 9,380,934 B2 | 6/2016 | Sugiura et al. |
| 9,730,578 B2 | 8/2017 | Lai |
| 2003/0117580 A1 | 6/2003 | Franz et al. |
| 2006/0026051 A1 | 2/2006 | Rose |
| 2009/0228299 A1 | 9/2009 | Kangarloo et al. |
| 2010/0123875 A1 | 5/2010 | Gemoules |
| 2012/0095349 A1 | 4/2012 | Peyman |
| 2013/0100410 A1 | 4/2013 | Liang |
| 2014/0129259 A1 | 5/2014 | Seriani |
| 2015/0070650 A1 | 3/2015 | Seriani |
| 2016/0098528 A1 | 4/2016 | Seriani |
| 2017/0027445 A1 | 2/2017 | Isogai |

FOREIGN PATENT DOCUMENTS

| | | |
|---|---|---|
| WO | 2008150476 A1 | 12/2008 |
| WO | 2011034638 A1 | 3/2011 |
| WO | 2013081619 A1 | 6/2013 |
| WO | 2013105915 A1 | 7/2013 |
| WO | 2014/074157 | 5/2014 |

OTHER PUBLICATIONS

International Search Report for PCT/US2017/050761.
Petition for Post-Grant Review (PGR2018-00100) with respect to parent application U.S. Pat. No. 9,980,644 filed by 20/20 Vision Center, LLC on Sep. 14, 2018.
European Search Report in European Application No. 17851355.2, dated Apr. 7, 2020, 7 pages.
Karpecki, et al. "New Techs for Your Specs," Review of Optometry, vol. 146, No. 04 Issue Apr. 15, 2009, 3 pages.
Vasr™ "Voice Assisted Subjective Refractor," retrieved from www.vm.vmaxvision.com/vasr on Nov. 26, 2018, 2 pages.
Author Unknown, "PSF technology shows promise," Ophthalmology Times, Sep. 18, 2013, 1 page.
Karpecki, et al. "Time to Replace the Phoropter?" Review of Optometry, Issue Jun. 15, 2012, 4 pages.
Tanabe, et al., "A Remote Operating Slit Lamp Microscope System," Methods Inf Med 2011; 50: 427-434.
K. Go, et al. "Designing a Remote-Control Slit Lamp Microscope for Teleophthalmology," WISH 2010, Apr. 11, 2010, pp. 65-68 pages.
K. Go, et al., "Eye, Robot: A Network Control System for Ophthalmologic Examination," APCHI 2008, LNCS 5068, pp. 48-57, 2008.
Remote Controlled Slit-Lamp Biomicroscope Soon to Be a Reality, Ophthalmic Biophysics Center, Bascom Palmer Eye Institute University of Miami School of Medicine, Florida Lions Eye Bank, Annual Report 2010, 16 pages.
Charukamnoetkanok, et al., "Robotic Slit-lamp for Tele-Ophthalmology," ICROS-SICE Int'l Joint Conf. 2009, Aug. 18-21, 2009, Fukuoka Int'l Congress Center, Japan, 5 pages.
Karp, Andrew, "Educating the Patient," Vision Monday, Apr. 16, 2012, retrieved from www.visionmonday.com, 2 pages.
Cole, Jane, "Your Phoropter on Steroids?" Review of Optometry, Issue Sep. 15, 2017, 7 pages.
*20/20 Vision Center, LLC*, v. *Dicataloptometrics LLC*, "Final Written Decision", Case PGR2018-00100, U.S. Pat. No. 9,980,644 B2, dated Apr. 15, 2020, 49 pages.

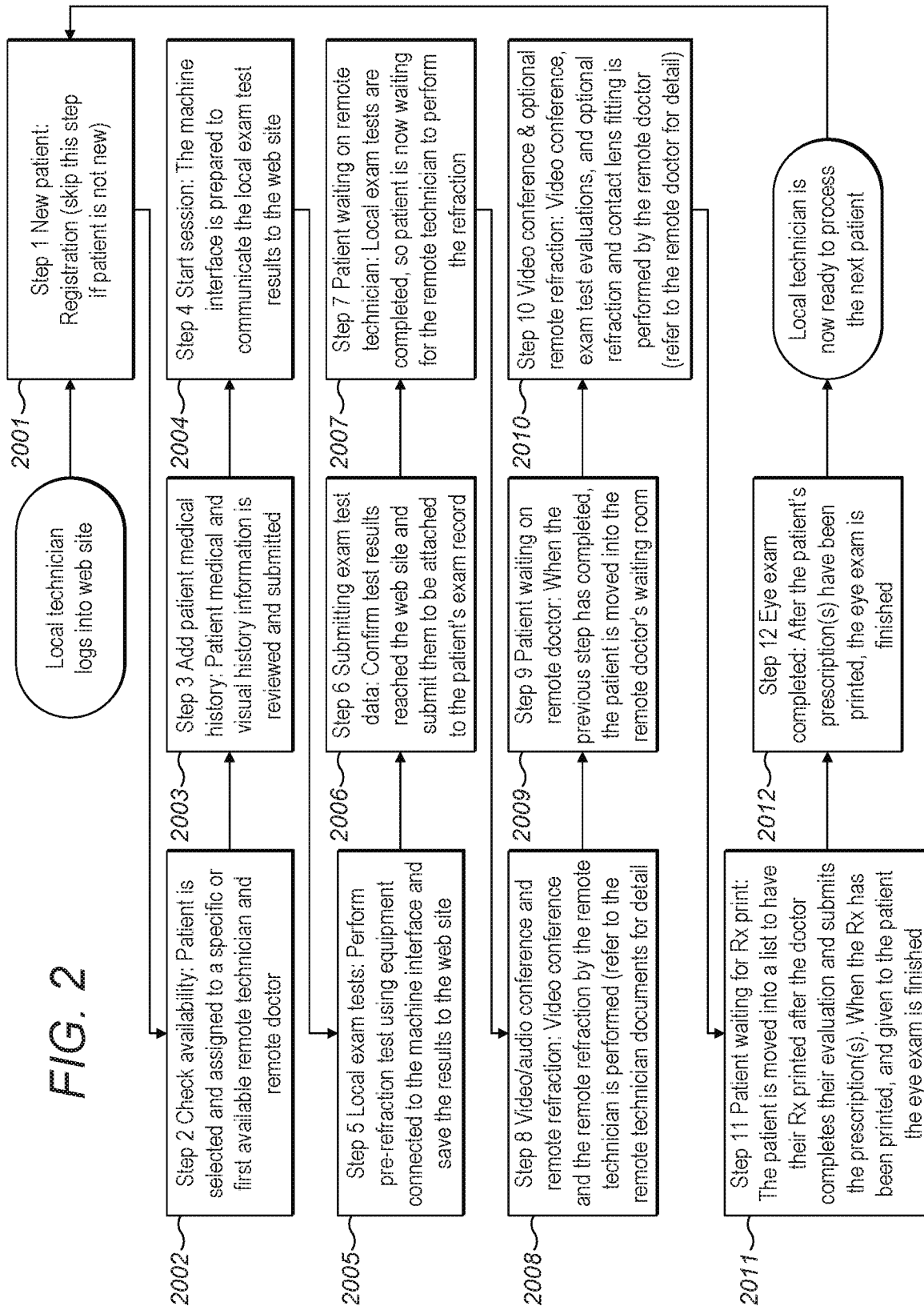

FIG. 5

REMOTE COMPREHENSIVE EYE EXAMINATION SYSTEM

RELATED APPLICATION

This application is a continuation-in-part of U.S. patent application Ser. No. 15/916,639, filed on Mar. 9, 2018, which is a continuation of U.S. patent application Ser. No. 15/699,533, filed on Sep. 8, 2017, now U.S. Pat. No. 9,980,644, which claims the benefit of U.S. Provisional Patent Application Ser. No. 62/394,369 filed on Sep. 14, 2016.

FIELD OF THE DISCLOSURE

The present disclosure relates generally to an apparatus, method, and system for remote comprehensive eye examinations. This apparatus, method, and system may also be usefully configured to work in various other arts beyond remote comprehensive eye examinations.

BACKGROUND

Comprehensive eye examinations need to become more accessible in the U.S., since over 75% of adults use some form of vision correction. But many areas have a limited supply of optometrists and ophthalmologists—the gatekeepers for eye examinations—or such supply may be reduced during certain days and hours of the week. Access to comprehensive eye examinations is critical in determining not only corrective prescriptions for eyeglasses and contact lenses, but also in identifying potential diseases of the eye and body, such glaucoma, macular degenerations, and hypertension.

The internet is being increasingly utilized for optical products such as eyeglasses and contact lenses. Further, there are new technologies that offer the consumer refractions via smartphones, portable devices, as well as through the internet on a computer in order to determine the patient's prescription. Companies and devices that currently offer this technology via refraction devices include: Opternative, Smart Vision Labs, Eyenetra, Peek, Pediavision, and 2win.

But these refraction-based systems do no provide the patient/consumer with a comprehensive eye examination. While these systems update their prescription for eyeglasses and/or contact lenses with a device, they are not able to discover other potential ocular health issues. Indeed, the reduction of vision in the eye and therefore the necessity for eyeglasses and/or contact lenses is the stimulus that motivates a patient/consumer to see an eyecare professional. Thus, patients that use present-day internet-based tools for glasses or contacts will not be evaluated for other ocular-related medical issues and will not normally schedule such visits with an optometrist or ophthalmologist. Without such visits, important ocular issues could be missed and go undiagnosed. Although extremely convenient, the use of these new technologies without proper medical guidance may results in adverse effects for patients, and ultimately cause more harm than good.

Accordingly, it is therefore desirable to combine the convenience of internet or remote based eye testing with the availability of skilled optometrists or ophthalmologists into an apparatus, method, and system for remote comprehensive eye examinations.

SUMMARY OF THE INVENTION

Embodiments of the present disclosure call for a remote station where an optometrist or ophthalmologist need not be required to be on-site to perform a comprehensive eye examination. Instead, an ophthalmic technician is present with the patient in the exam room to operate eye examination equipment and transmit patient information to remote location. At that remote location, a skilled technician is present to provide the necessary optical and/or medical care, and may operate the phoropter from the remote location if he/she desires. Using video and/or teleconferencing equipment and a phoropter located in the patient examination room along with management software, the system works to determine the final optical prescription for the patient. That information, coupled with findings from other devices which are integrated with the management software, and that the patient uses locally, are reviewed by a remote based optometrist or ophthalmologist.

While the patient is being evaluated for eyeglasses or contacts, the optometrist or ophthalmologist may also operate the phoropter located in the patient examination room from the remote location if he/she desires and evaluate the patient for other ocular-related medical issues. Once the findings are finalized by the optometrist or ophthalmologist remotely, the final prescription for eyeglasses and/or contact lenses, along with any additional comments or findings, will print locally at the examination location and be delivered to the patient.

The advantages of this remote station-based approach are widespread.

Patients benefit from the remote station because it provides them with a method to obtain needed eye care at a time and location that is convenient to them. Patients also benefit from the peace of mind that a skilled optometrist or ophthalmologist will be evaluating them and checking for ocular issues beyond the need for eyeglasses or contacts.

The optometrist or ophthalmologist benefits by being able to provide his or her services at times and places of his or her choosing (not unlike the way a driver works for ride-sharing services, such as Uber, at times convenient to him or her). Further, the potential pool of patients for the optometrist or ophthalmologist is much larger since he or she is not limited to the market of patients within driving distance of his or her office.

The host at the local side of the remote station, where patients are present, benefit because the services offered by the system allow for better utilization and synthesis of other parts of the host's business. For example, a retail optical store will often lose sales if a customer requires a prescription to purchase eyeglasses and there is no optometrist or ophthalmologist in the store to write the prescription. But it is impractical and expensive to have an optometrist or ophthalmologist available during the many hours that a retail optical store needs to be open in order to make a profit. This is even more so in the case of an optical department for a large retailer, such as Walmart or Target, where the retailer may be open 18 to 24 hours per day. Hosting a remote station that provides access to an optometrist or ophthalmologist at any needed time, day or night, significantly enhances the profitability of the optical store or optical department.

In addition, the present invention is designed to comply with the recommendations related to telemedicine as set forth by the American Optometric Association (AOA). It is believed that no other prior system meets all such recommendations for comprehensive eye examinations that include subjective refractions with professional judgement by a doctor for an accurate objective refraction.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

FIG. 2 is a flowchart showing the workflow of a local technician for remote comprehensive eye examinations, in accordance with some embodiments.

FIG. 5 is a the controller menu that may be used by the remote doctor to remotely operate a phoropter, in accordance with some embodiments.

Figure 1:
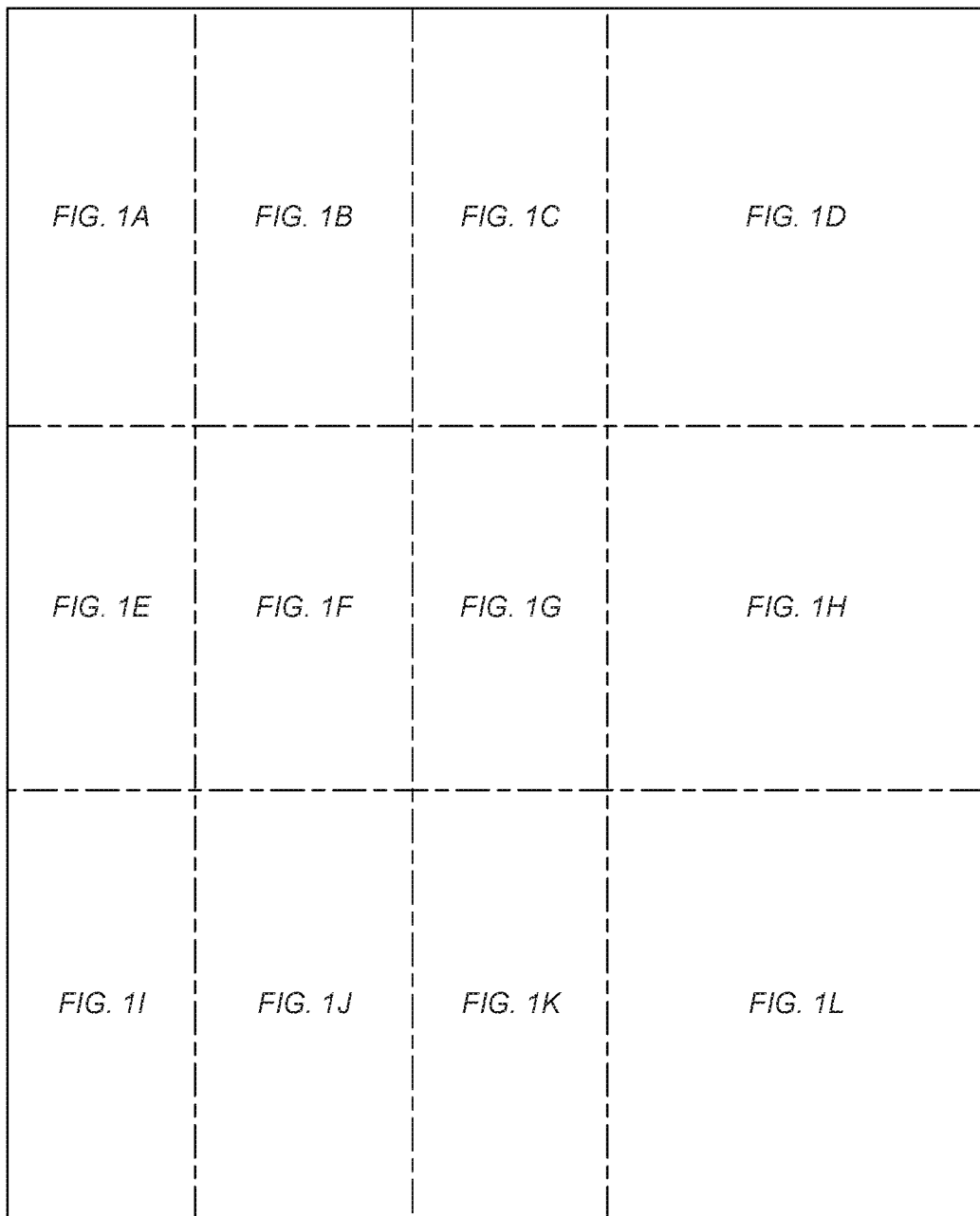
FIG. 1 (consisting of FIGS. 1A, 1B, 1C, 1D, 1E, 1F, 1G, 1H 1I, 1J, 1K and 1L) is a system diagram of an apparatus, method, and system for remote comprehensive eye examinations, in accordance with some embodiments.
Figure 1A:
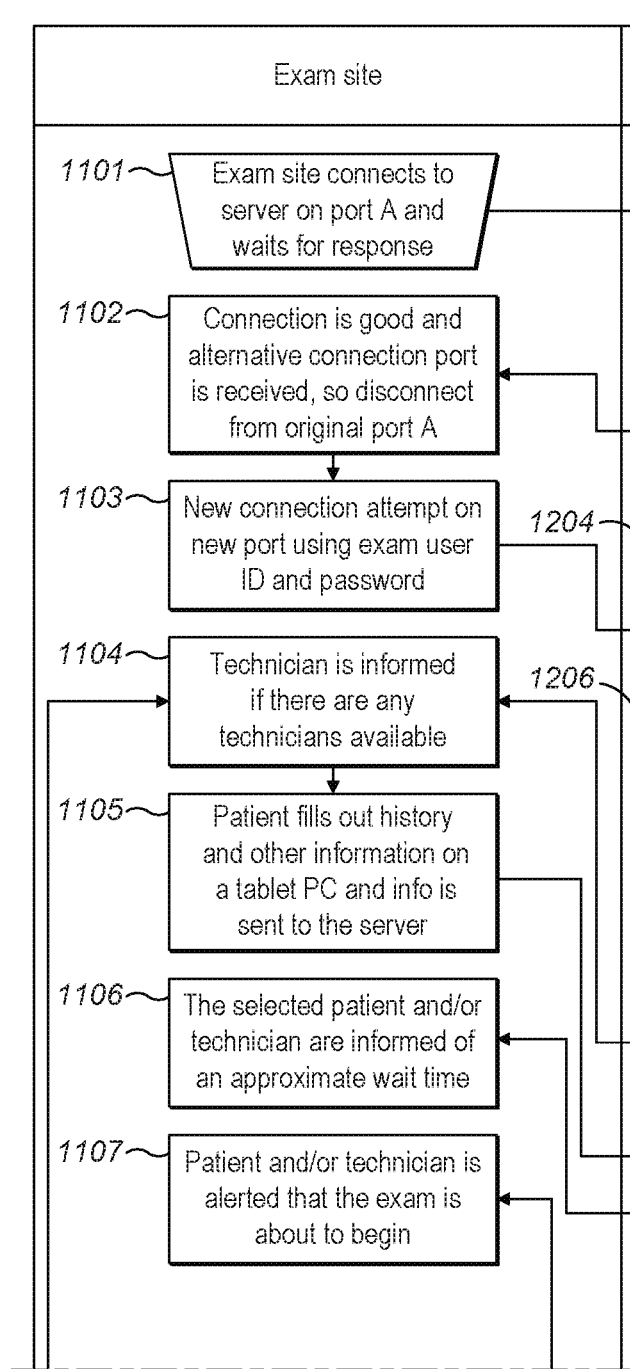
Figure 1B:
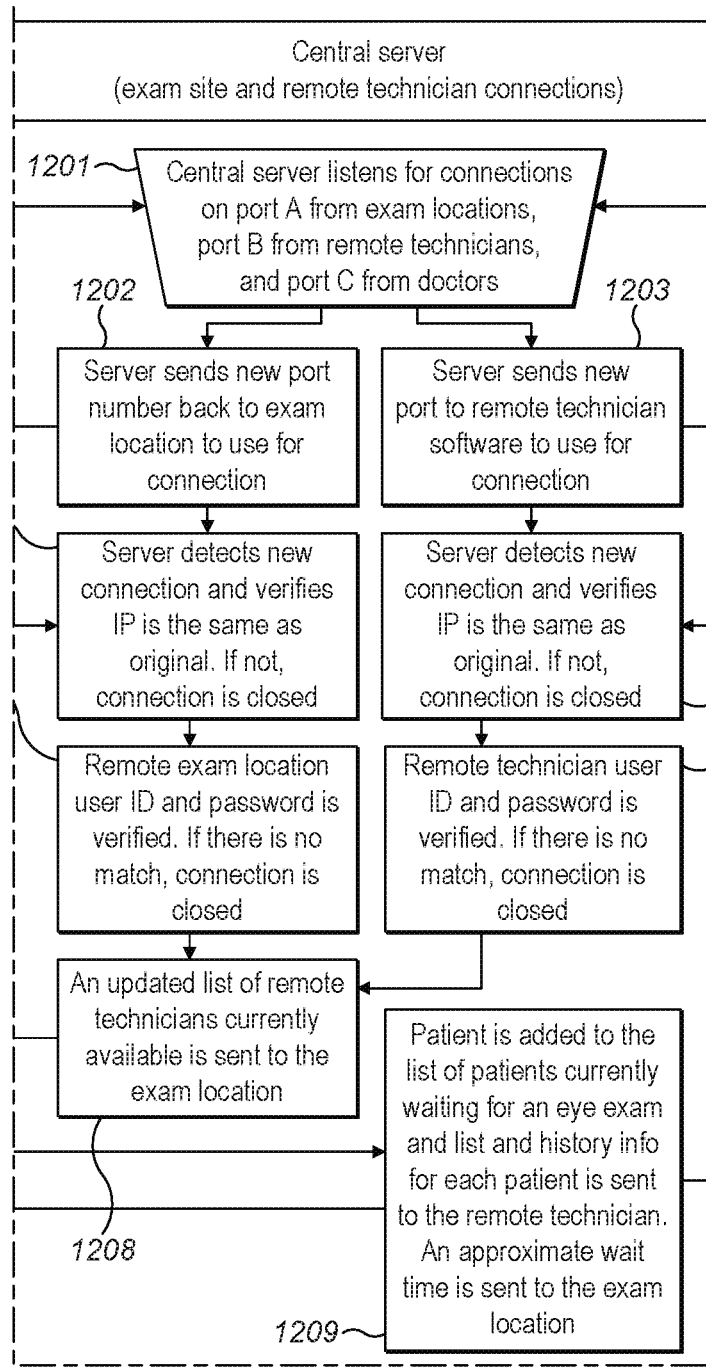
Figure 1C:
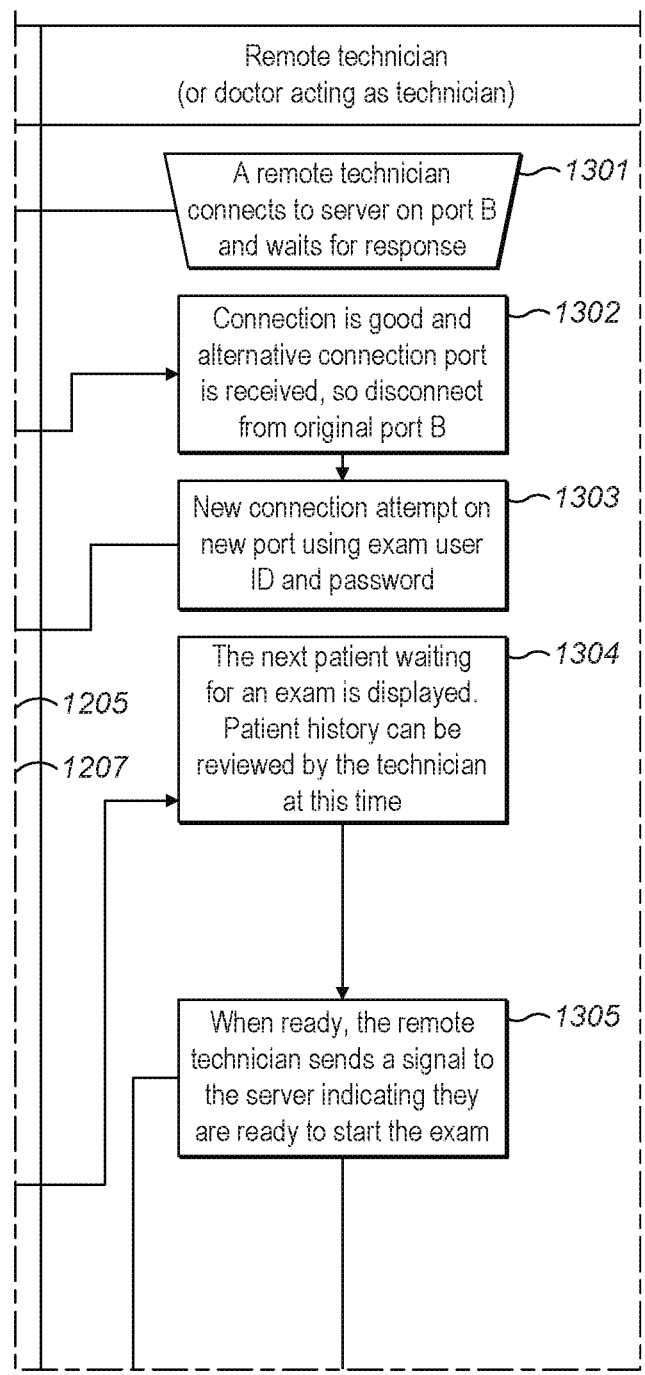
Figure 1D:
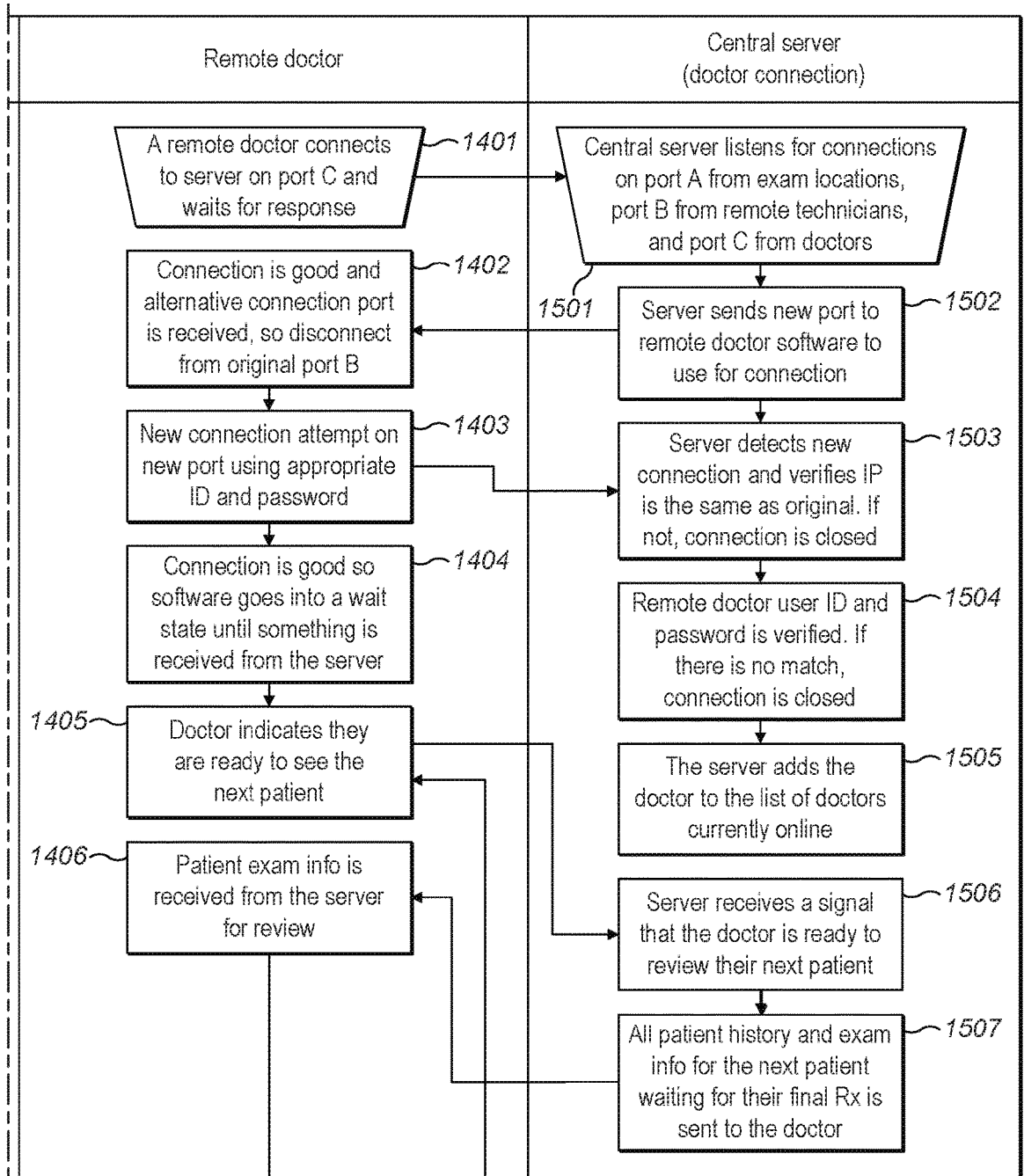
Figure 1E:
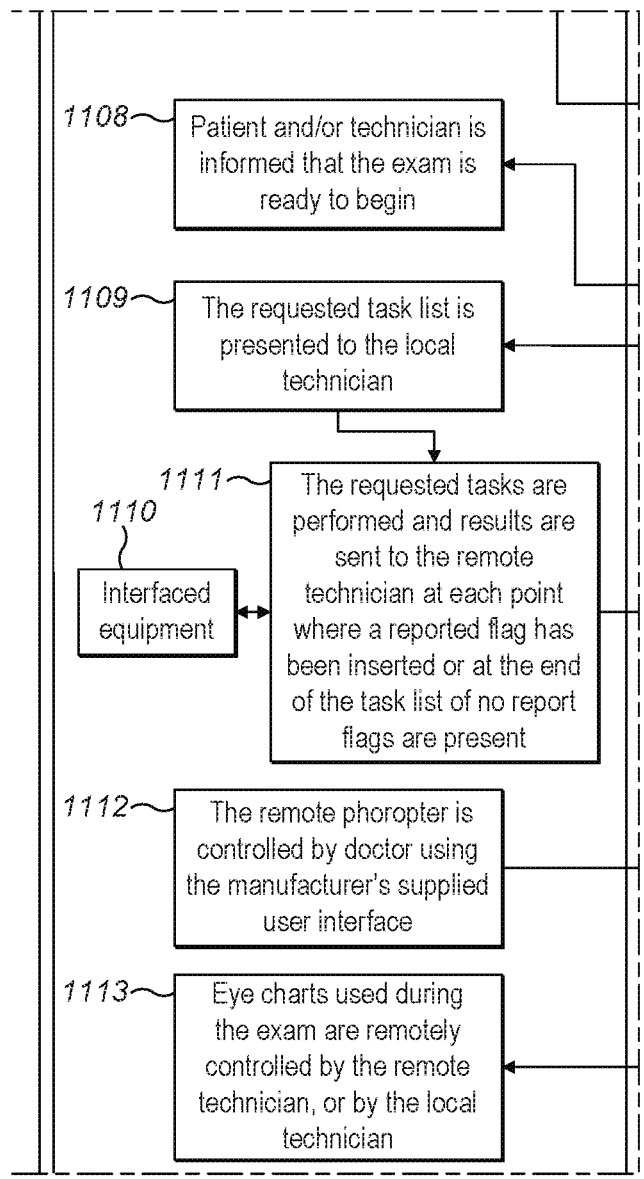
Figure 1F:
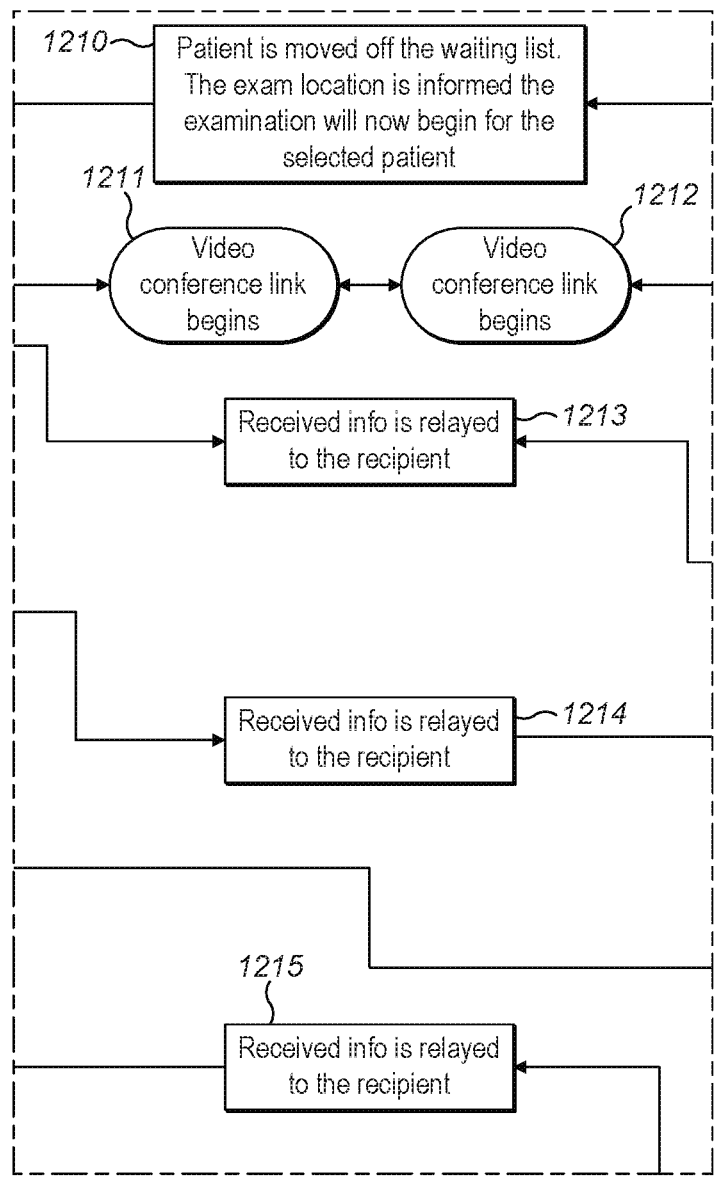
Figure 1G:
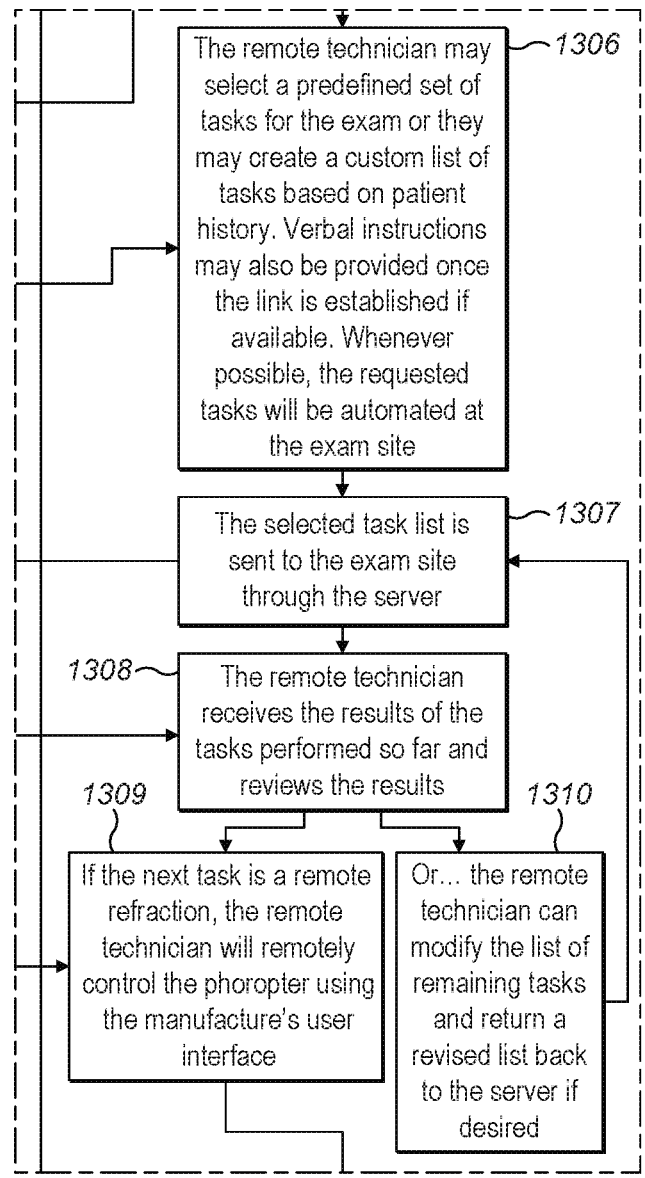
Figure 1H:
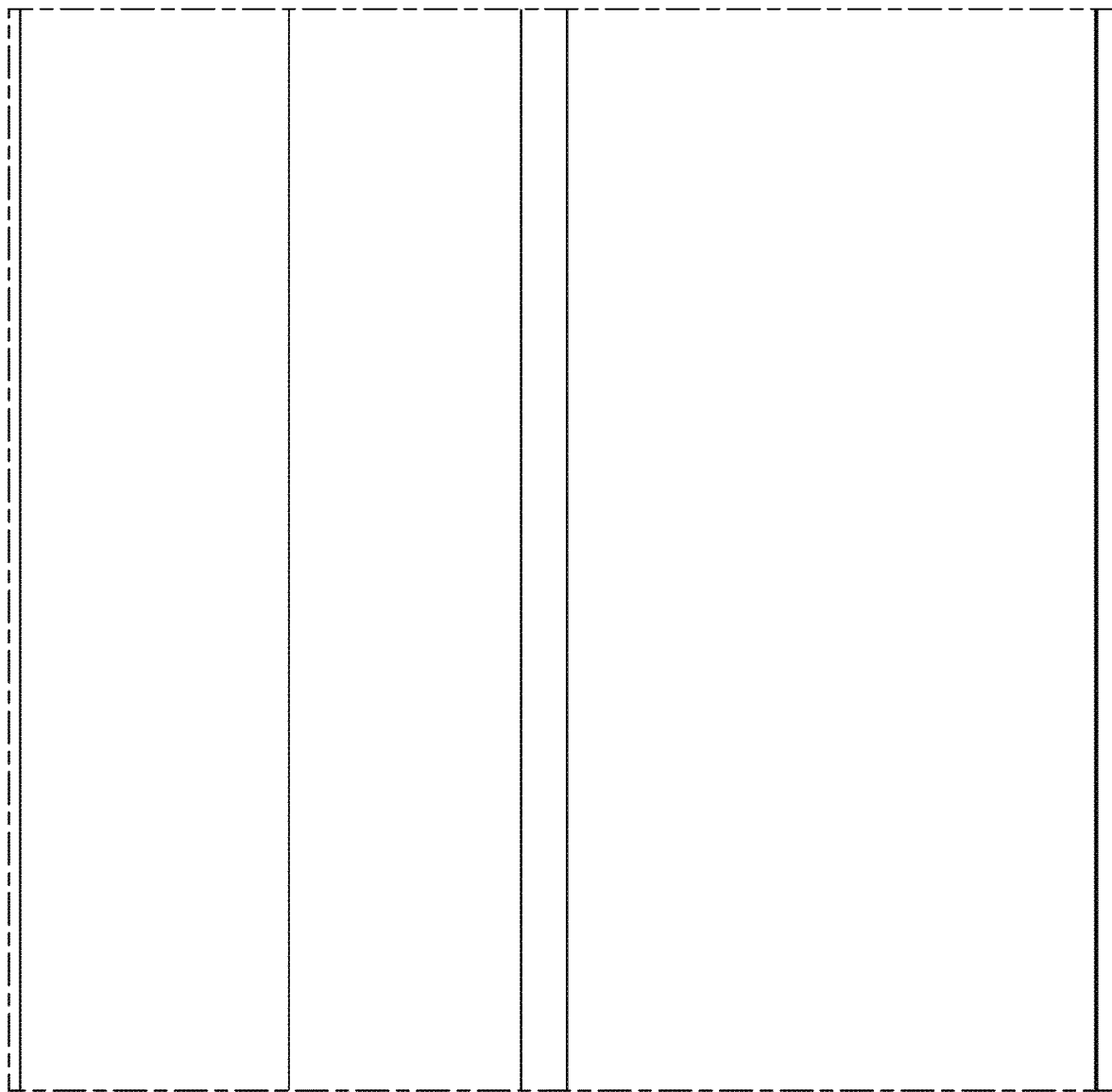
Figure 1I:
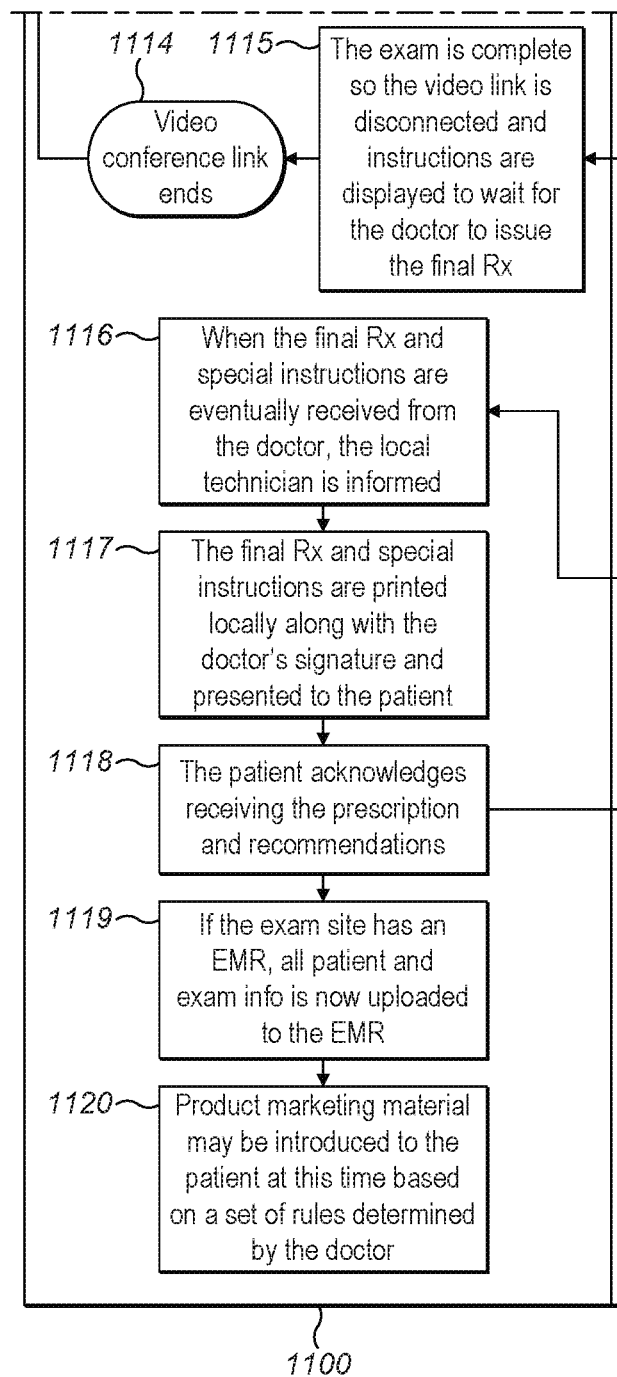
Figure 1J:
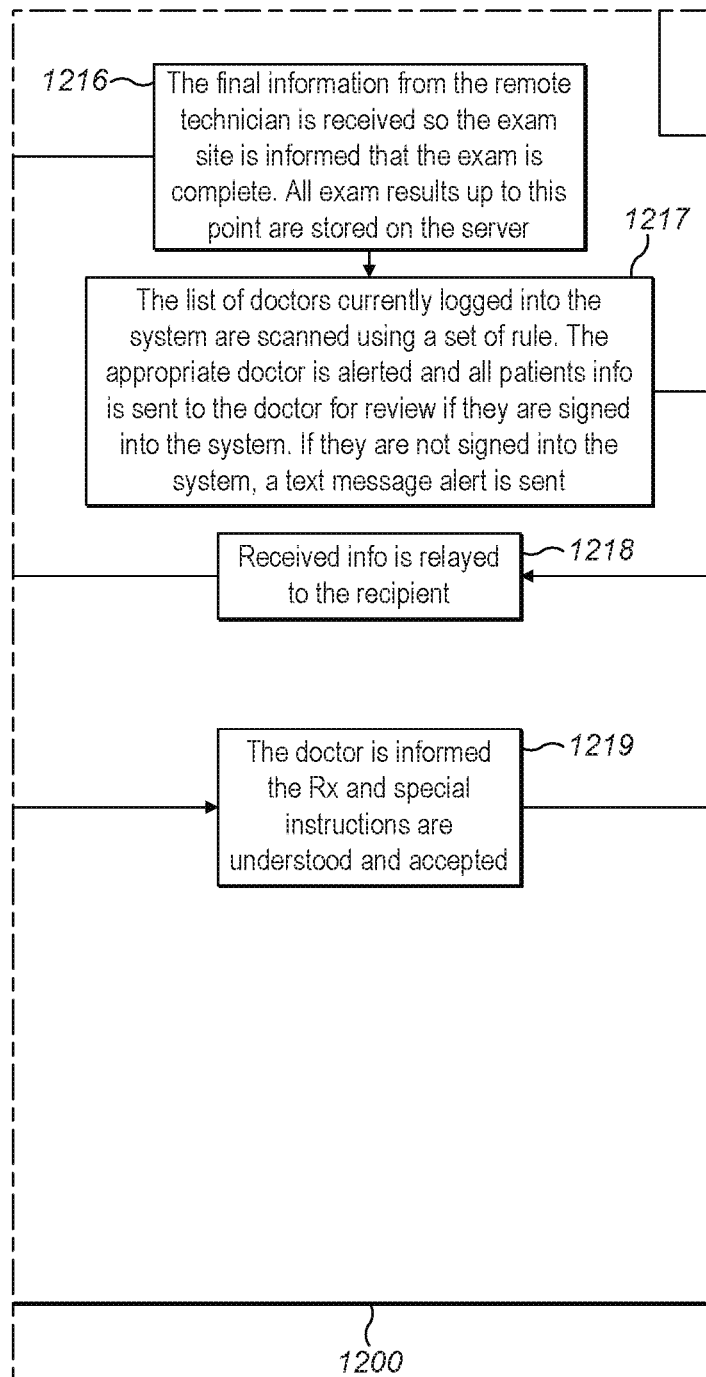
Figure 1K:
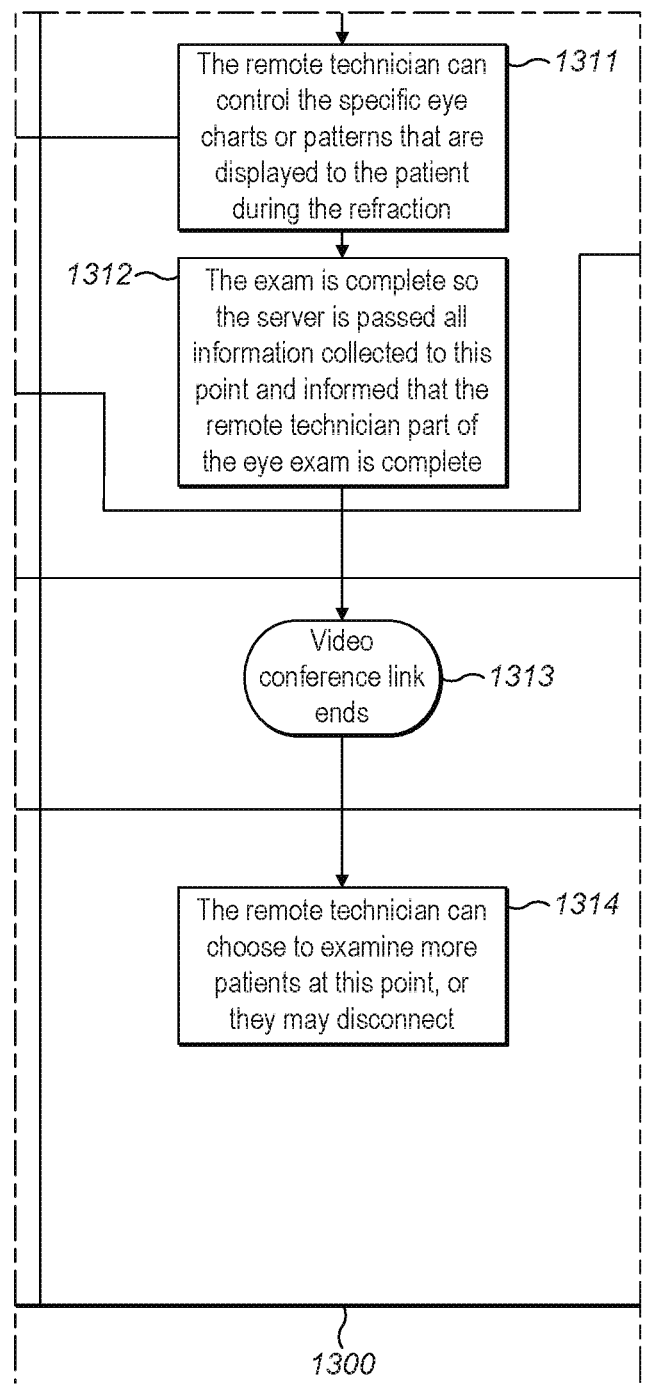
Figure 1L:
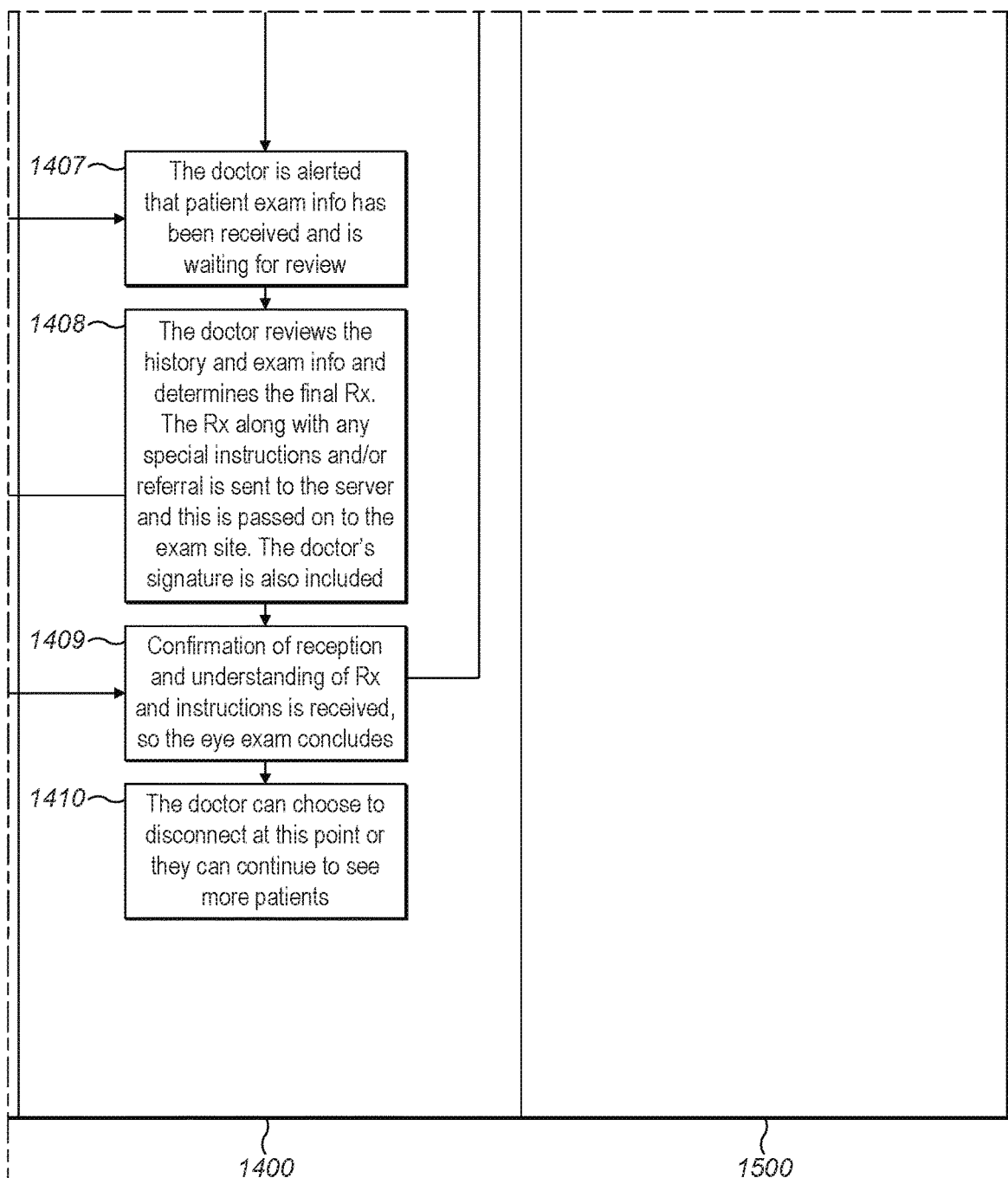

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

I. Compliance with Recommendations of the American Optometric Association

A. Comprehensive Eye Examination Requirements

The present invention is designed to collect all of the information and perform all of these tests set forth by the AOA for a comprehensive eye health examination and vision analysis. Such requirements are set forth below.

1. Chief Complaint: assessment of the patient's reason for getting an eye exam.

2. General Physical Health History: complete health history to screen for physical conditions and medications that may affect eyesight.

3. General Ocular Health History: complete eye health history including family history of eye conditions, disease, or medication.

4. External and Internal Eye Health Evaluation: examination for the signs of eye disorders, including cataracts and other eye disorders.

5. Current Prescription Analysis: evaluation of current lens prescription, if applicable.

6. Visual Acuity: test for the eyes' ability to see sharply and clearly at all distances.

7. Refraction: test for the eyes' ability to focus light rays properly on the retina at distances and close by.

8. Tonometry: test to measure internal fluid pressure of the eye (increased pressure may be an early sign of glaucoma).

9. Visual Coordination: check for external eye muscle balance and coordination.

10. Accommodative Ability: test of the eyes' ability to change focus from distance to near.

Prior telemedicine schemes have not been designed to accomplish all of the above tasks. Indeed, many provide only refractive services.

B. Optimal Platforms for Telemedicine

In addition to the above, the present invention is designed to comply with the recommendations of the AOA with respect to optimal telemedicine requirement—live interactive eye and vision telehealth services. Per the AOA, "live interactive eye and vision telehealth services" are those that use videoconferencing as a core technology. Participants are separated by distance, but interact in real-time. In contrast "store-and-forward" eye and vision telehealth services refers to a method of providing asynchronous consultations to referring providers or patients. A history and a set of images are collected at the point of service and are transmitted for review by an eye doctor. In turn, the eye doctor provides a consultative report back to the referring provider or patient at the point of service. "Eye and vision remote patient monitoring services" refers to personal health and medical data collected from an individual in one location via electronic communication technologies, which is transmitted to a provider in a different location for use in care coordination and related support.

The present invention is also designed to comply with the recommendations of the AOA for optimal uses of technology in synchronous telehealth uses. Per the AOA, for synchronous telehealth uses, a controlled environment, including adequate lighting, and a high resolution video camera is typically required at the originating site, and a monitor with resolution matched to the camera resolution is required at the distant site. Videoconferencing systems work optimally when a high-speed connection speed is used. Slower connection speeds may necessitate that the individual presenting the patient perform either still image capture or freeze frame to render a quality image. For asynchronous uses, a controlled environment, including adequate lighting, and a digital camera with a high pixel resolution is typically required. For systems that transmit over the Internet, secure encryption and multi-factor authentication are recommended. Remote patient monitoring solutions often take the form of software as a service, with clinical software that allows eye doctors and other clinical staff to manage patient populations by exception. Direct-to-patient eye and vision health-related applications, including online vision tests and other mobile eye and vision-related applications, must also comply with the above requirements.

The present invention is designed to comply with the recommendations of the AOA regarding credentialing and privileging. Per the AOA, the Joint Commission (TJC) has implemented standards for telehealth/telemedicine. Under the TJC telemedicine standards, practitioners who render care using live interactive systems are subject to credentialing and privileging at the distant site when providing direct care to the patient. The originating site may use the credentialing and privileging information from the distant site when certain requirements are met. Doctors who render services using store-and-forward systems are viewed by TJC as "consultants" and might not be required to be credentialed at the originating site. However, standards can vary by state and organization.

The present invention is also designed to comply with the recommendations of the AOA regarding privacy and confidentiality. Per the AOA, practitioners who provide eye and vision telehealth services should ensure compliance with the Health Insurance Portability and Accountability Act of 1996 (HIPAA), as amended, and its implementing regulations. The handling of records, faxes, and communications is subject to the same HIPAA standards as those that apply in a standard office environment. For asynchronous telehealth uses, HIPAA compliance largely relies on the originating site informing patients that their information will be traveling by electronic means to another site for consultation. This should be noted in the consent form at the point of service, and the HIPAA notice of privacy practices. In addition, all electronic transmissions should be encrypted and reasonable care should be taken to authenticate those providers who have electronic access to the records.

The present invention is also designed to comply with the recommendations of the AOA regarding licensing. Per the AOA, interactive telehealth requires the equivalent of direct patient contact. In the U.S., telehealth using interactive technologies is generally restricted to jurisdictions where the eye doctor is permitted, by law, to practice. In other words, the provider using interactive technologies is typically required to be licensed to practice in the jurisdiction in which the patient is located. For store-and-forward applications, most states require telehealth providers to be licensed in the same state in which the patient resides, even when he or she acts only as a consultant. Doctors of optometry and other appropriate, licensed providers who wish to provide store-and-forward consultations across state lines should limit such consultations to originating states in which they are permitted, by law, to provide care.

The present invention is also designed to comply with the recommendations of the AOA with respect to responsibility/liability. Per the AOA, if direct services (doctor-to-patient) are provided (no assistance at the referring site), the consulting eye doctor bears full responsibility (and potential liability) for the patient's care. The diagnostic and therapeutic recommendations rendered are based solely on information provided by the patient. Therefore, any liability should be based on the information available at the time the consult was answered. In a consultative model (doctor-to-doctor), liability may be shared; however, the allocation of responsibilities will vary on a case-by-case and state-by state basis. Doctors of optometry and other appropriate, licensed providers should verify that their liability insurance policy covers telehealth/telemedicine services, including those services provided across state lines, if applicable, prior to the delivery of any such service.

C. Criteria for High-Quality Eye and Vision Telehealth Services

The AOA supports the use of eye and vision telehealth services provided by licensed eye doctors—doctors of optometry and ophthalmologists—and other appropriate, licensed professionals in certain instances, and supports coverage of and payment for eye and vision telehealth services, when several important criteria are met. The present invention is designed to meet certain of the AOA's criteria as set forth below.

1. The standard of care must remain the same regardless of whether eye and vision telehealth services are provided in-person, remotely via telehealth, or through any combination thereof. Doctors may not waive this obligation, or require patients to waive their right to receive the standard of care. Further, a payor may not require either the doctor or patient waive the right to receive the standard of care.

2. The use of eye and vision telehealth services may be appropriate for standard basic data acquisition, gathering repetitive specific data, confirmation of expected therapeutic results, confirmation of stability/or homeostasis, and notifications of changes in chronic conditions. Further uses may be appropriate as new evidence and technologies are made available.

3. The use of eye and vision telehealth services is not appropriate for establishing the doctor-patient relationship, for an initial diagnosis, as a replacement for recommended face-to-face interactions, or as a replacement for partial or entire categories of care.

4. Eye doctors and other licensed professionals delivering eye and vision telehealth services must be licensed in the state in which the patient receives services (subject to respective laws and regulations), and must abide by that state's licensure laws and regulations.

5. Patients must be made aware of potential limitations of the services that can be provided via telehealth. Eye doctors or other licensed professionals delivering eye and vision telehealth services must, when clinically appropriate, promptly refer patients for an in-person diagnosis and/or care.

6. Patients or referring practitioners seeking eye and vision telehealth services must have a choice of eye doctor, if possible, and must have access, in advance, to the licensure and qualifications of the clinician providing services. The delivery of eye and vision telehealth services must be consistent with state scope of practice laws in the state in which the patient is located at the time of the encounter.

7. The patient's relevant health history must be collected as part of the provision of eye and vision telehealth services. Appropriate health records should be available to the consulting eye doctor prior to or at the time of the telehealth encounter. Consulting eye doctors should have a good understanding of the culture, health care infrastructure, and patient resources available at the site from which consults are originating. The provision of eye and vision telehealth services must be properly documented. These health records should, when appropriate, be available at the consultant site and at the referral site.

8. The provision of eye and vision telehealth services should include care coordination with the patient's primary care provider, and eye doctor, if one exists. This coordination should include, at a minimum, identifying the patient's primary care provider and eye doctor in the eye and vision telehealth services referral record, and providing a copy of the health record to those members of the treatment team who do not have electronic access to it. This provision is especially important so that information regarding diagnoses, test results, and medication changes are available to the care team.

9. Organizations and clinicians participating in eye and vision telehealth services should have an ongoing training program and current list of required criteria for both the distant and receiving sites. In addition, those programs that are using eye and vision telehealth services should have documentation of their training programs for any technician who is capturing clinical images and for any clinician who is providing consults. Each organization should also maintain documentation on how the program protects patient privacy, promotes high-quality clinical and image data, continuity of care, and care coordination for patients who may request or require subsequent in-person evaluations or procedures.

10. While monitoring patients remotely, the regular interaction between clinical care coordination staff, patients, and their eye doctor(s) and other primary care providers is critically important for successful outcomes. Only FDA-approved devices being utilized in the manner for which they were approved may be used to monitor patients remotely. The risks and benefits of medical devices should be properly and thoroughly weighed through science and evidence to ensure efficacy and quality and to protect the public health.

11. Organizations and clinicians participating in eye and vision telehealth services must have protocols for local referrals (in the patient's geographic area) for urgent and emergency services. Mechanisms to facilitate continuity of care, follow-up care, and referrals for urgent and emergency services in the patient's geographic area must be in place. Any new prescriptions must be communicated directly to the patient's care team (unless the team has easy electronic access to the eye and vision telehealth record).

12. When creating directories of participating eye doctors for establishing network adequacy, an insurer may not consider access to eye and vision telehealth services as a substitute for locally available doctors of optometry, who can offer a wide range of eye health and vision care services.

13. The AOA supports eye and vision telehealth services designed and dedicated to provide demonstrably high-quality patient care. The AOA does not support eye and vision telehealth services primarily focused on offering access to prescriptions without conducting an adequate history, examination, patient diagnosis, and/or valid and proper doctor-patient relationship.

14. With respect to the doctor-patient relationship:

(a) For eye and vision telehealth services where a referring provider ultimately manages the patient (including prescriptions), the consulting eye doctor is not required to have a pre-existing, valid doctor-patient relationship. It is optimal, however, if the patient has available access to in-person follow-up with a local eye doctor when needed.

(b) For live interactive eye and vision telehealth services and direct-to-patient eye and vision health-related applications, including online vision tests and other mobile eye and vision-related applications, the consulting eye doctor must either: (i) Have an existing doctor-patient relationship (having previously seen the patient in-person); or (ii) Before providing services, establish communication with the patient's existing care team, including the patient's eye doctor, in order to document eye, vision, and systemic history, past comprehensive eye and other examinations, and any related patient diagnosis; or (iii) Be a part of an integrated health delivery system where the patient already receives care, in which the consulting eye doctor has access to the patient's existing medical record and can coordinate follow-up care.

15. The use of direct-to-patient eye and vision-related applications, including online vision tests and other mobile eye and vision-related applications, raise several additional issues (and all of the above criteria still apply):

(a) Direct-to-patient eye and vision-related applications, based on current technologies and uses, cannot replace or replicate in-person comprehensive eye examination provided in-person by an eye doctor.

(b) The eye health portion of a comprehensive eye examination and the refractive portion of a comprehensive eye exam, based on current technologies and uses, cannot be replaced or replicated by direct-to-patient eye and vision-related applications.

(c) Screening for specific or groups of eye health issues using telehealth for direct-to-patient eye and vision-related applications, based on current technologies and uses, should not be used to diagnose eye health conditions or as a replacement or replication for a comprehensive dilated eye exam. Screenings solely identify risk, which is a risk that only an in-person comprehensive eye examination can begin to valuate, mitigate, and/or address.

(d) Refractive tests, including online vision tests and other mobile vision-related applications, cannot be, based on current technologies and uses, used to provide a refractive diagnosis and/or an eyeglass or contact lens prescription, due, in part, to these tests not currently including a controlled testing environment, subjective refraction, or professional judgement. Additionally, self-administered vision tests, based on current technologies and uses, cannot be relied on as accurate for an objective refraction.

(e) Photographs obtained by patients, their family members, or their friends outside of a clinical setting may not be of adequate quality, or may not include the information needed to make an accurate diagnosis.

II. Workflow for Remote Comprehensive Eye Examination

Turning to FIG. 1, shown is an overall system workflow diagram for an apparatus, method, and system for remote comprehensive eye examinations. Shown are workflows for the exam site 1100, central server (exam site and remote technician connection) 1200, remote technician 1300, remote doctor 1400, and central server (remote doctor connection) 1500.

The exam site workflow 1100 may initiate a connection to the central server (exam site and remote technician connection) 1200 on a specified port and wait for a response 1101. Similarly, the remote technician 1300 may initiate a connection to the central server (exam site and remote technician connection) 1200 on a specified port and wait for a response 1301. In both of these cases, the central server (exam site and remote technician connections) 1200 may also be listening for connections on specified ports from exam sites and remote technicians 1201, which may be different ports for exam sites and remote technicians. In the case of the exam site initiated connection, the central server (exam site and remote technician connection) 1200 may send a new port number back to the initiating exam site 1100 to use for the connection 1202. The exam site 1100 may receive this new port number from the central server (exam site and remote technician connection) 1200 and disconnect from the original port number 1102. Now, the exam site 1100 may initiate a new connection to the central server (exam site and remote technician connection) 1200 using the new port provided by the central server (exam site and remote technician connection) 1200 and using an exam user ID and password 1103. The central server (exam site and remote technician connection) 1200 may detect the new connection from the exam site 1100 over the updated port number and checks the IP address. If the IP address is the same as original exam site 1100 IP address, then the connection may be kept open. If the IP address is different, then the connection may be closed 1204. If the IP address is the same, and the connection is kept open, then the central server (exam site and remote technician connection) 1200 may verify the exam user ID and password. If the credentials don't match an existing account, then the connection may be closed. If the credentials do match an existing account, then connection may be kept open 1206.

Similar to the case with the exam site, if the central server (exam site and remote technician connection) 1200 receives a connection from the remote technician 1300, the central server (exam site and remote technician connection) 1200 may send a new port number to the initiating remote technician 1300 to use for the connection 1203. The remote technician 1300 may receive this new port number from the central server (exam site and remote technician connection) 1200 and disconnect from the original port number 1302. Now, the remote technician 1300 may initiate a new connection to the central server (exam site and remote technician connection) 1200 using the new port provided by the central server (exam site and remote technician connection) 1200 and using an remote user ID and password 1303. The central server (exam site and remote technician connection) 1200 may detect the new connection from the remote technician 1300 over the updated port number and checks the IP address. If the IP address is the same as original remote technician 1300 IP address, then the connection may be kept open. If the IP address is different, then the connection may be closed 1205. If the IP address is the same, and the connection is kept open, then the central server (exam site and remote technician connection) 1200 may verify the remote user ID and password. If the credentials don't match an existing account, then the connection may be closed. If the credentials do match an existing account, then connection may be kept open 1207.

Once the remote user and site has been verified, the central server (exam site and remote technician connection) 1200 may send an updated list of remote technicians 1208 currently available to the exam site 1100. The exam site 1100 technician may be informed if there are any technicians currently available 1104.

At the exam site 1100, the patient may fill out their history and other information on a tablet PC or other medium, and that information 1105 may be sent to the central server (exam site and remote technician connection) 1200. The central server (exam site and remote technician connection) 1200 receives this patient information, and the patient may be added to the list of patients currently waiting for an eye exam. The patient list and history information for each patient may be sent to the remote technician 1300 and the approximate wait time 1209 may be sent to the exam site 1100. At the exam site 1100, the selected patient and/or technician are informed of an approximate wait time 1106. At the remote technician 1300, the next patient waiting for an exam may be displayed, and patient history may be reviewed by the technician 1304. When the remote technician 1300 is ready, they may send a signal to the central server (exam site and remote technician connection) 1200 indicating that they may be ready to start the exam 1305. At the central server (exam site and remote technician connection) 1200, the patient may be moved off the waiting list, and the exam site 1100 may be informed that the examination may now begin for the selected patient 1210. At the exam site 1100, the patient and/or technician may be informed that the exam is about to begin 1107. At the remote technician site 1300, the remote technician may select a predefined set of tasks for the exam or they may create a custom list of tasks that may be based on the patient's history. Verbal instructions may also be provided once the video link is established if available. Whenever possible, the required tasks may be automated 1306 at the exam site 1100. At the central server (exam site and remote technician connection) 1200, the video conference may link 1211, 1212 the remote technician 1300 and exam site 1100. At the exam site 1100, the patient and/or technician is informed that the exam may be ready to begin 1108. Video conference data may flow between the exam site 1100 and remote technician 1300 through the central server (exam site and remote technician connection) 1200. The task listed selected by the remote technician 1300 may be sent 1307 through the central server (exam site and remote technician connection) 1200 to the exam site 1100. The central server (exam site and remote technician connection) 1200 relays 1213 this information to the exam site 1100. At the exam site 1100, the requested task may be presented to the local technician 1109. The requested tasks may be performed and results may be sent to the remote technician 1300 at each point where a reported flag has been inserted or at the end of the task list if no report flags are present 1111. During this phase, the system may interact 1110 with equipment at the exam site 1100. The central server (exam site and remote technician connection) 1200 receives information and relays 1214 it to the remote technician 1300. The remote technician 1300 may receive they results of the tasks performed so far and may review the results 1308. If the task is a remote refraction, the remote technician 1300 may remotely control the phoropter using the manufacturer's user interface 1309. At the exam site 1100, the remote phoropter may be controlled by the remote technician 1300 using the manufacturer's user interface 1112. Alternatively, the remote technician 1300 may modify the list of remaining tasks and return a revised list back to the central server (exam site and remote technician connection) 1200 if desired 1310. This revised task list may be sent to the exam site 1100 through 1307 the central server (exam site and remote technician connection) 1200. During the remote phoropter exam, the remote technician 1300 may control the specific eye charts or patterns that are displayed to the patient during the refraction 1311. The central server (exam site and remote technician connection) 1200 relays this control information 1215 to the exam site 1100. At the exam site 1100, eye charts used during the exams may be remotely controlled by the remote technician 1300 or by the local technician 1113.

At the conclusion of the exam, the central server (exam site and remote technician connection) 1200 is passed all of the information collected to this point and is informed that the remote technician 1300 portion of the eye exam is complete 1312. The final information from the remote technician 1300 is received by the central server (exam site and remote technician connection) 1200 and the exam site 1100 may be informed that the exam is complete. All exam results to this point 1216 may be stored on the central server (exam site and remote technician connection) 1200. At the exam site 1100, the exam is completed, and the video conference link may be disconnected and instructions may be displayed to wait for the doctor to issue the final prescription 1115. The video conference link may be disconnected 1114 and the exam site 1100 is informed if there are any remote technicians 1300 currently available for another session 1104. At the remote location 1300, the video conference link may end 1313. The remote technician 1300 may choose to examine more patients at this point, or they may disconnect 1314. If they choose to examine more patients, they may be informed of the next patient waiting for an exam by central server (exam site and remote technician connections) 1200 and patient history can be reviewed by remote technician 1300 1304.

The remote doctor 1400 may initiate a connection to the central server (doctor connection) 1500 on a specified port and wait for a response 1401. The central server (doctor connection) 1500 may also be listening for connections 1501 on specified ports from remote doctors 1400. The central server (doctor connection) 1500 may send a new port number back to the initiating remote doctor 1400 to use for the connection 1502. The remote doctor 1400 may receive this new port number from the central server (doctor connection) 1500 and disconnect from the original port number 1402. Now, the remote doctor 1400 may initiate a new connection to the central server (doctor connection) 1500 using the new port provided by the central server (doctor connection) 1500 and using a user ID and password 1403. The central server (doctor connection) 1500 may detect the new connection from the remote doctor 1400 over the updated port number and checks the IP address. If the IP address is the same as original remote doctor 1400 IP address, then the connection may be kept open. If the IP address is different, then the connection may be closed 1503. If the IP address is the same, and the connection is kept open, then the central server (doctor connection) 1500 may verify the user ID and password. If the credentials don't match an existing account, then the connection may be closed. If the credentials do match an existing account, then connection may be kept open 1504. The central server (doctor connection) 1500 may then add the remote doctor 1400 to the list of doctors currently online 1505. At the remote doctor 1400, once the connection is established and verified by the central server (doctor connection) 1500, the software may go into a wait state 1404 until something is received from the central server (doctor connection) 1500. The remote doctor 1400 may indicate that they are ready to see the next patient 1405. The central server (doctor connection) 1500 may receive a signal that the remote doctor 1400 is ready to review their next patient 1506. All patient history and exam information for the next patient waiting for their final prescription is sent 1507 to the remote doctor 1400 by the central server (doctor connection) 1500. The remote doctor 1400 may receive the patient information from the central server (doctor connection) 1500 for review 1406.

At the central server (exam site and remote technician connections) 1200, the list of doctors currently logged into the system may be scanned using a set of rules. The appropriate doctor may be alerted and all patient information may be sent to the remote doctor 1400 for review if they are signed into the system. If they are not signed into the system, a text message or similar medium may be sent 1217. The remote doctor 1400 may be alerted that patient information has been received and is waiting for review 1407. The remote doctor 1400 may review the patient history and exam information and may determine the final prescription. The prescription, along with any special instructions and/or referral information is sent to the central server (exam site and remote technician connections) 1200, which is then passed on to the exam site 1100. The remote doctor's 1400 signature or other authorization may also be included 1408. The central server (exam site and remote technician connections) 1200 receives this information 1218, and relays it to the exam site 1100. The exam site 1100 may be notified when the prescriptions and/or any special instructions are received from the remote doctor 1400 through the central server (exam site and remote technician connections) 1200 so that the local technician may be notified 1116. The final prescription and/or any special instructions may be printed locally along with the doctor's signature or other authorization and presented to the patient 1117. The patient may acknowledge receiving the prescription and/or recommendations 1118. The remote doctor 1400 may be informed through the central server (exam site and remote technician connections) 1200 that the prescription and/or special instructions have been understood and accepted 1219. The remote doctor 1400 may receive this confirmation of reception and understanding of prescription and information, and concludes the eye exam 1409. The remote doctor 1400 may choose to disconnect at this time, or they may continue to see more patients 1410. If they decide to see more patients they may indicate that they are ready to see the next patient 1405.

At the exam site 1100, if the exam site has electronic medical records (EMR), all patient and exam information may be uploaded to the EMR 1119. Product marketing material may be introduced to the patient at this time based on a set of rules determined by the doctor 1120.

The system may also contain a combination hardware and automatic software switch that allows the eye exam equipment to be used by this remote comprehensive eye exam system, or by an on-site doctor to do a standard non-remote eye exam. The method of switching the equipment from one mode to the other may be accomplished at the exam site through the use of a single physical hardware switch.

The machine interface software automatically detects whether a local or remote exam is being done and directs the received output from the exam devices to the appropriate user-selectable location(s) at the appropriate time and in the preferred user selectable format. The user-selected data format can be in the form of file(s) that are dropped into a shared network folder or the selected data format can be output through a configurable serial port.

This hardware switching feature saves the exam site a significant amount of money because it allows the same eye exam equipment to be used for both local and remote exams—a unique feature of this system. This avoids the need for the exam site to purchase one set of eye exam equipment for non-remote eye exams and another set of equipment for remote exam use.

III. Features of Remote Comprehensive Eye Examination

The potential features of the remote comprehensive eye examination apparatus, method, and system are listed below. Any or all of these features may be used in various combinations.

A. Server Features

1. Configuration and Setup Menu

The configuration and setup menu may have the following features:

a. The server Configuration/Maintenance/Setup menu(s) will be user and password protected.

b. Enter, edit, and delete all info and passwords for exam sites, remote technicians, and remote doctors.

c. Enter, edit, and delete pricing groups that can be assigned to any user or groups of users.

d. Create and edit rules based on things such as groups, insurance, exam site, remote technician and doctor location.

e. Record all exam activity (Exams started, exams completed, who did what, how long it took, etc.).

f. Set and edit exam fees linked to specific groups.

g. Set and edit exam fees for each individual location that is not assigned to a group or insurance carrier.

h. Allow optional volume discounts to a specific user or group i. Automatically produce reports and statements at a given interval or on request.

j. Automatically email reports and statements at a given interval or on request.

k. Allow high level user to add adjustments to any statement.

2. Connection and Storage.

a. Implement all server logic as defined in the flowchart.

b. Initial connection and handshake with port info to exam site, remote technician, and remote doctor software.

c. User ID, password, and IP verification on every final connection.

d. Handle multiple simultaneous connections from exam sites, remote technicians, and remote doctors.

e. Handle multiple simultaneous communication links between specific exam sites, remote technicians, and doctors.

f. Logic to pair the most appropriate remote technician and/or doctor with the patient based on rules.

g. Transmission encryption.

h. Disk storage encryption.

i. Video conferencing software will be used for the video link.

3. Communications a. Send pass-through commands from the remote technician to the exam site to control an interfaced phoropter for the refraction (May not be needed if the digitally controlled phoropter comes with its own remote interface from the manufacturer).

b. Send pass-through commands from the remote technician to the exam site to control an interfaced eye chart.

c. Maintain a current list of all exam sites currently connected d. Maintain a current list of all remote technicians currently connected.

e. Maintain a current list of all remote doctors currently connected.

f. Send a current list of connected exam sites to the remote technician when requested.

g. Send a current list of connected remote technicians to the exam site when requested.

h. Send a current list of connected remote doctors to the remote technician when requested.

i. Send a current list of connected remote doctors to the exam site when requested.

j. Send a current list of remote doctors not connected but marked as available to the exam site when requested.

k. Send a current list of remote doctors NOT connected but marked as available to the remote technician when requested.

l. Send a text alert to a remote doctor that is not connected but marked as available.

m. Relay information from the exam site to the remote technician as needed, perhaps using a Digital Imaging and Communications in Medicine (DICOM) protocol.

n. Relay information from the remote technician to the exam site as needed, perhaps using a DICOM protocol.

o. Relay information from the remote technician to the remote doctor as needed, perhaps using a DICOM protocol p. Relay information from the remote doctor to the exam site as needed, perhaps using a DICOM protocol.

q. Relay information from the exam site to the remote doctor as needed, perhaps using a DICOM protocol.

r. Accept and act on supported server commands from the exam site.

s. Accept and act on supported server commands from the remote technician.

t. Accept and act on supported server commands from the remote doctor.

u. Send pass-through commands on to the intended recipient (exam site, remote technician, or remote doctor).

v. Send an estimate the time remaining before a particular patient's exam can begin based on previous exam completion times.

w. DICOM protocol to be used if possible to relay information between the exam site, remote technician, and remote doctor. Some examples of what this may include are:

i. Visual acuity (without glasses, with current glasses, with new Rx, etc.).

ii. Current glasses prescription.

iii. Patient information and history.

iv. Results from equipment interfaced at the exam site.

v. Keratometer readings (K readings).

vi. Cornea Topography.

vii. Autorefractor readings (Rx).

viii. Fundus photography (photos).

ix. Slit lamp (may be photos or video).

x. Manual or interfaced Phoropter results (Rx).

xi. Other interfaced Equipment.

xii. Other objective test results.

xiii. Other subjective test results.

B. Exam Site Development

1. Configuration and Setup Menu a. The exam site software will need to have a password protected setup/configuration menu.

b. Enter, edit, or delete all exam site users and passwords c. Enter and edit server IP and server connection port.

d. Enter and edit ID and password to use for server login.

e. Define the interfaced machines that are available at the exam site and define their function(s).

f. Define the manual operated machines that are available at the exam site and define their function(s).

g. Enter, edit, or delete rules that determine what if any products will be presented and recommended after the exam is finished.

h. Setup will need an option to allow exporting the cumulative exam results when the exam is completed to a specific EMR.

i. Have an option to assign the preferred remote technician for exams when available.

2. Connections and Storage a. Implement all server logic as defined in the flowchart.

b. Initial connection and handshake and receive the reconnect port info from the main server.

c. Reconnect on the specified port for the final connection with the server.

d. Send the exam site's user ID and password for login.

e. Transmission encryption.

f. Disk storage encryption.

g. Video conferencing software may be used for the video link.

3. User Interface (May be a Dual-Monitor System)

a. Monitor A will be used for accessing the setup menu and for interaction as needed with the exam site technician.

b. A second monitor may be optionally used for interaction as needed with the exam site patient.

c. Note that separate software may be used on a tablet at the exam site to collect information from the patient prior to the exam 4. Communications a. Retrieve the collected patient information from the tablet computer over the local area network.

b. Send patient information and history to the remote technician.

c. Send supported server commands to the server and wait for a response.

d. Send supported remote technician commands through the server and wait for a response.

e. Send supported remote doctor commands through the server and wait for a response ("Rx accepted" is one).

f. Receive commands from the server and act on the command appropriately ("Task list" is one).

g. Note that if the phoropter at the exam site does not come with a remote interface from the manufacturer, an interface between the remote technician and the machine will have to be developed.

h. Note that if there is a need for the remote technician to control the eye chart at the exam site during the refraction, an interface between the remote technician and the eye chart device will have to be developed. Equipment interface commands from the server will need to be passed through to the intended equipment.

i. Receive the final Rx from the doctor through the server and print it locally. It will contain the doctor's signature along with any special instructions or recommendations.

j. After the final Rx is received and the exam is done, the system will look at any and all rules that are present regarding product promotion and will then present the appropriate product info (if any) to the patient.

C. Remote Technician Site Development

1. Configuration and Setup Menu a. Each technician will have their own copy of this software and it will be installed on a separate computer or separate folder on the same computer so there will be no need to handle multiple technicians and multiple passwords in this software.

b. The remote technician software will need to have a password protected setup/configuration menu.

c. Enter, edit, or delete the remote technician's info.

d. Enter and edit the server IP and server connection port.

e. Enter and edit ID and password to use for the server login for this remote technician.

f. Enter, edit, or delete tasks that the technician can choose from if they need to design a custom list of exam tasks for a specific patient. This list should be stored in a separate file that can be easily copied to another technician's computer.

g. Define one or more named lists of pre-set tasks the technicians can choose from when doing the examination. Each item in the named list will be placed in the list in the same order it will need to be performed during the actual eye exam.

h. Have an option to enter, edit, or delete a list of preferred remote doctors to choose from and notify if available when the technician completes the exam.

i. Have an option to enter, edit, or delete a list of exam locations that the technician is limited to when doing a remote exam. A checkbox for "No Limit" or "Allow All" should also be available that would allow the technician to do an exam at any exam site that has specified that this technician can do their exams.

j. Setup configuration may be needed for any remotely interfaced exam equipment such as a remotely controlled phoropter or eye chart.

2. Connections and Storage a. Implement all remote technician logic as defined in the flowchart.

b. Initial connection and handshake and receive the reconnect port info from the main server.

c. Reconnect on the specified port for the final connection with the server.

d. Send the remote technician's user ID and password for login.

e. Transmission encryption.

f. Disk storage encryption.

g. Video conferencing software will be used for the video link, but it is unclear if or how it will need to be interfaced.

3. User Interface (May be a Dual-Monitor System).

a. The menu system will contain a user interface that allows the technician to perform all tasks as defined in the flowchart.

b. The menu system will allow the remote technician to view and select from a list of patients currently waiting for an eye exam.

c. The menu system will allow the remote technician to view the patient info and history for any patient in their selection list prior to selecting a patient and starting an exam.

d. The menu system will allow the remote technician to choose from a named list of pre-set tasks to use when doing the exam, or they may design a custom list using the list of tasks that have been created in the setup menu.

e. Depending on how the video conferencing software in integrated with this system, the video conferencing software may be started from the technicians menu.

f. When the exam site has finished all tasks and the remote refraction is complete, all information collected so far about the patient and from all equipment is sent through the server to the remote technician where it can be viewed in a menu system. The remote technician may either be sent any of the photos and/or video that may be collected during the exam, or just the values collected from each task. The doctor receives everything.

g. The menu system needs an option that allows the remote technician to tell the exam site that the exam is complete and ready to go to the doctor for final Rx. The remote technician should be allowed to add their own comment to the signal and this comment will be added to the total data collected at the exam site.

h. The menu needs an option to terminate the exam and to specify a reason.

4. Communications a. Send supported server commands to the server and wait for a response.

b. Send supported remote technician commands through the server to the exam site and wait for a response.

c. Receive supported commands from the server and act on the command appropriately.

d. Receive supported data from the exam site through the server and act on the info appropriately.

e. Pass remotely interfaced equipment commands to the exam site through the server.

f. Support for all communications related items defined in the flowchart that are not covered.

D. Remote Doctor Development

1. Configuration and Setup Menu a. Each doctor will have their own copy of this software and it will be installed on a separate computer or separate folder on the same computer so there will be no need to handle multiple doctors and multiple passwords in this software module.

b. The remote doctor software will have a password protected setup/configuration menu.

c. Enter, edit, or delete the remote doctor's information.

d. Enter and edit the server IP and server connection port.

e. Enter and edit ID and password to use for the server login for this remote doctor.

f. Allow entering all doctor information (name address, license, business name, contact phone numbers, email, text #, etc.).

g. Allow storing a digital copy of the doctor's signature.

h. Allow doctor to specify if they want to be alerted via text if and when they are not online and an Rx is waiting to be finalized by them.

i. Have an option to enter, edit, or delete a list of exam locations that the doctor will be limited to when finalizing an Rx. A checkbox for "No Limit" or "Allow All" should also be available that would allow the doctor to finalize an Rx at any exam site that has specified that this doctor can finalize their exams.

2. Connection and Storage a. Implement all remote doctor logic as defined in the flowchart, above.

b. Initial connection and handshake and receive the reconnect port information from the main server.

c. Reconnect on the specified port for the final connection with the server.

d. Send the remote doctor's user ID and password for login.

e. Transmission encryption.

f. Disk storage encryption.

3. User Interface (May be a Dual-Monitor System).

a. The menu system will contain a user interface that allows the remote doctor to perform all tasks as defined in the flowchart, above.

b. Receive and display an alert of some kind if at least one Rx is waiting for this doctor's approval.

c. The menu system will allow the remote doctor to view and select from a list of patients currently waiting to have their Rx finalized.

d. The menu system will allow the remote doctor to view the patient info and history for any patient in their selection list prior to selecting a patient and starting the process of finalizing the Rx.

e. The selected patient's info, history, and all data collected during the exam should be available to view from the menu system. The information collected will include values collected during each exam task, but it may also include photos and video which should also be viewable from the menu system.

f. When the doctor has reviewed all the available information, they will make a determination about what the final Rx should be. The menu system needs to have a way for the doctor to enter the final Rx info along with any comments, recommendations, or special instructions they might want to pass on to the patient. If the doctor sees a condition that needs a referral, they may decide not to issue an Rx and to simply send referral info in the special instructions.

g. There is a button to allow sending everything needed to print the final Rx at the exam site. This includes the doctor's name, business name, address, phone, possibly email, state license number, final Rx, instructions, and a digital copy of the doctor's signature.

4. Communications a. Send supported server commands to the server and wait for a response.

b. Send supported exam site commands through the server to the exam site and wait for a response.

c. Receive supported commands from the server and act on the command appropriately.

d. Receive supported data/commands from the exam site through the server and act on the info appropriately.

e. Support for all communications related items defined in the flowchart that are not covered above.

IV. System Operations

The following provides a comprehensive description of role of each participant in the apparatus, method, and system for remote comprehensive eye examinations: the patient, the local technician, the remote technician and the remote doctor. The patient may be assigned to a local eyecare technician, where the patient and the local eyecare technician are located at a local diagnostic center. The patient is then assigned to a remote eyecare technician (possibly by the local technician), where the remote eyecare technician is located at a first remote diagnostic center. The patient is finally assigned (possibly by the local technician) to a eyecare doctor, where the eyecare doctor is located at a second remote diagnostic center, which may or may not be the same remote diagnostic center as the first remote diagnostic center. Thus, in some embodiments, the eyecare doctor, the remote technician and the local technicians are in different locations.

A. The Patient

The patient portal and kiosk is a hand-held tablet computer with custom software that is used by the patient during the examination process. This tablet can be used to update the patient medical history, view the current exam status, and also view previous prescriptions. The tablet will also provide links to various websites and videos which can be used to educate and entertain the patient while in the waiting area.

1. New Patient

When a new patient arrives at the doctor's office, the local technician will need to begin the process of gathering information about that patient to properly complete the examination. A vital step in this process is providing a kiosk tablet to the patient for them to fill out forms requesting patient information.

The local technician needs to start the process on the kiosk tablet of adding a new patient.

The local technician will need to click "Add Patient" to start the processing of adding a new patient into the system. When this button is clicked, the local technician Login Details dialog is displayed.

In this dialog, the technician will enter their username and password, which is also used to login to the patient portal. After this information has been properly entered, the kiosk tablet will present a page requesting patient information. It is at this point that the technician would hand the tablet off to the patient, asking the patient to fill-in the online forms.

The following images display the form that the patient will fill-out on the kiosk tablet. This form contains information such as name, address, birthdate, insurance information, signature, etc. Also, this form will allow the viewing of the Terms and Conditions and Privacy Policy, for the patient's approval.

After the patient completes filling in the patient information and clicks the "Submit" button, the patient will be shown the login screen, where they can login to the patient dashboard. Details of the patient dashboard are contained in the following section.

2. Existing Patient

The patient will login to the patient portal, by filling in their username and password on the dialog as illustrated in the following image.

When the patient logs into the system for the first time, they will be presented with the following dialog, where they will need to agree to the Terms and Conditions and Privacy Policy to continue using the patient portal.

At this point, the patient is now logged into the patient portal. From the patient portal, the patient can view the current exam status, review previous prescriptions, update personal information (address, phone number, etc.), and update their medical history, among other items.

When the patient logs into the patient portal, the patient dashboard will be presented. The dashboard contains information about the current exam status for the patient. The following shows the dashboard, with no patients currently waiting for an examination.

There are 4 main sections to the patient dashboard. As the patient moves through each phase of the examination process, the appropriate sections of the dashboard will be updated. From this dashboard, the patient can view the status of various aspects of the examination.

Before the examination, the patient should update their medical history, by selecting the "Add Medical History" button along the left-hand side of the screen. This will display the following form, which asks various questions about the patient's medical history.

3. Local Technician Status

When an examination is starting for the patient, the dashboard will change to display data similar to the following screen capture. The status is displayed as waiting for the local technician exam to begin.

Once the local technician has begun the exam process, the status on the patient dashboard will be updated accordingly. In the following image, the patient's status has been updated to local technician exam in progress, indicating that the patient is currently being examined by the local technician.

After the local technician's examination has completed, the patient will be passed to the remote technician. While the remote technician is performing the refraction, the patient's dashboard will be updated with a status indicating that the remote technician exam is in progress. The dashboard will update to reflect the current status when the remote technician exam has completed, and the patient is waiting for the remote doctor.

While the doctor is examining the patient, the dashboard is updated to reflect this status. When the exam has been completed, the patient dashboard will reflect the status.

4. Other Features

After one or more examinations have been completed on the patient, they can use the "View Prescription" button to view the current and any previous prescriptions.

The update profile option will allow the patient to change personal information, including such items as address, employer, insurance, etc. The information requested on this form is the same as the information requested during the initial patient session at the doctor's office.

The patient may desire to change their login password for the patient portal. The "Change Password" button will allow the password to be changed. To change the password, the patient must enter the old password, and then enter the new desired password with confirmation.

To enhance the patient experience, the kiosk tablet will provide opportunities for education and entertainment. This is achieved by giving the patient access to a select set of websites specifically chosen for patient enrichment. A button will be available on the menu in the patient portal called "Information", which when clicked will display a list of links that the patient is allowed to access.

There are 3 levels to the selection process for websites. First, the system may provide a list of websites that all patients will have the ability to access. Second, the group will be able to provide a list of websites that the patient may access. Third, the exam site can add more sites to which the patient should be granted access.

Typically, these sites will be educational (YouTube videos, lens suppliers, frame manufacturers, etc.). Access may also be granted to entertainment sites such as news, weather, and sports.

The kiosk hardware is a tablet computer that is configured to allow only one application to be run, and that is the custom kiosk software. When the kiosk is booted-up, the kiosk software will run automatically with no intervention required from anyone at the doctor's office.

The kiosk software is an application centered around a custom web browser, designed to give the patient access to a limited number of websites. The primary website that is available is the patient portal. This website provides information to the patient about current and previous examinations.

The portal will optionally allow patients to have access to external websites for educational and/or entertainment value, while waiting for an examination. The website available to the patient will be chosen by the group, and the exam site. To restrict the websites that are available to the patient, the kiosk software will occasionally request a whitelist from the portal server. This whitelist will then be used to block any website that is not on the whitelist.

The patient portal will also have a series of links, which will allow the patient to browse the permitted websites. The links are not available while the patient is initially setting up their profile on the system, but once the patient has setup their profile, the links will be made available.

To configure the allowed links and whitelist, the administrator, group, and site logins will have a configuration option available for setting these items on the website.

B. The Local Technician

The local technician in the system is always physically located at the exam site. The local technician takes care of registering the patient, collecting patient history, and walking the patient through the entire exam process. The local technician also performs the initial pre-refraction tests prior to the actual refraction by a remote technician and the final review by a remote doctor. Such tests may include non-contact tonometry glaucoma test, color blindness test, autorefractors and aberrometers.

If the patient is wanting contact lenses, the local technician may be directed by the remote doctor to ask the patient try on specific trial lenses, collect additional slit lamp images or videos with the trial lenses in place, and then attach the resulting media files to the patient's exam record so the remote doctor can verify the fit and make adjustments as needed.

If the local technician is unable to recall their login password or username, they can use the "Forgot Password?" or "Forgot Username?" recovery options as long as they still remember their email address. The recovery options will email the recovery instructions to the local technician's email address. If they are unable to recall their email address, they must contact the system administrator.

The local technician directly participates in a patient's eye examination and all results of the tests they perform at the exam site are reviewed by the remote doctor. The role of the local technician is primarily to observe the activity going on at their exam site and to maintain local technician information and occasionally patient information for their exam site.

1. Eye Examination Operations

The various steps of an eye exam that are performed by the local technician after they login are described below. The remote technician and remote doctor take over after the local technician has performed the pre-refraction tests. Their roles in the process are covered separately in the remote technician and remote doctor sections.

As shown in FIG. 2, the local technician performs the following steps.

Step 1: New Patient Registration 2001. This step is not required if the patient has ever had a previous eye exam done at an exam site in the same group as this exam site, otherwise the local technician must register the patient into the system. The demographic and patient medical and visual history information can be entered directly by the patient using a kiosk tablet, or the local technician can enter this information for them if the patient prefers during a private consultation.

If the patient entered this information themselves using a kiosk tablet, they can now log into their patient portal using the ID and password they just supplied. If the local technician entered all the patient information for them using the local technician's computer, the local technician can now log back into the web site normally.

Step 2: Check Availability 2002. This step is where the logged in local technician chooses the "Check Availability" menu option to select a patient and begin the eye exam process. Other patient search options are also available from the drop down list.

A local technician may determine that the patient wants to see the first available remote technician and remote doctor rather than waiting for a specific remote technician or remote doctor. The number of logged in remote technicians and remote doctors who can see this patient will be displayed after the selections have been made.

Alternatively, the local technician may searched for specific remote technicians or remote doctors based on skills, acceptance of the patient's insurance, and language. (Special note: Only doctors licensed in the state where the exam site is located will be allowed to see the patient.)

After the local technician is finished selecting the patient, and the remote technician and remote doctor choice has been selected, the local technician dashboard will appear.

Step 3: Patient Waiting for Local technician—Add Patient Medical History 2003. At this point, the local technician dashboard will automatically appear and the selected patient will now appear in the "Patient Waiting for Local Technician" list. The patient medical history should now be reviewed and attached to the current eye exam. If the patient updated their medical history through the patient portal prior to their eye exam appointment, this process will be as simple as verifying the current history information with the patient and clicking the "Submit" button. If the patient has not recently updated their history form through the patient portal, the local technician must consult with the patient and update the history info for them at this time.

After the patient medical history form has been completed, the local technician will click the "Submit" button and the local technician dashboard will once again appear.

Step 4: Patient Waiting for Local Technician—Start Session 2004. When the local technician is ready to begin the local exam tests for a specific patient, they will click that patient's "Start Session" button.

At this point, the machine interface software should be running in the background of the local technician's computer and they will click the "Send Patient ID" button. The machine interface will accept the patient ID sent by the web site and will bring itself to the front of the web browser and be ready to accept data from interfaced local exam machines. The machine interface will use the patient ID to identify all local exam tests performed during the current local exam test session.

Step 5: Local Exam Tests 2005. The local technician will now perform all required pre-refraction local exam tests for the current patient. The interfaced exam site machines will send the test results to the machine interface. When all local exam tests have been completed, the local technician will click the "Save All Exam Tests" button and all exam tests and associated media files will be sent to the web site and attached to the patient's current exam record.

Figure 3:
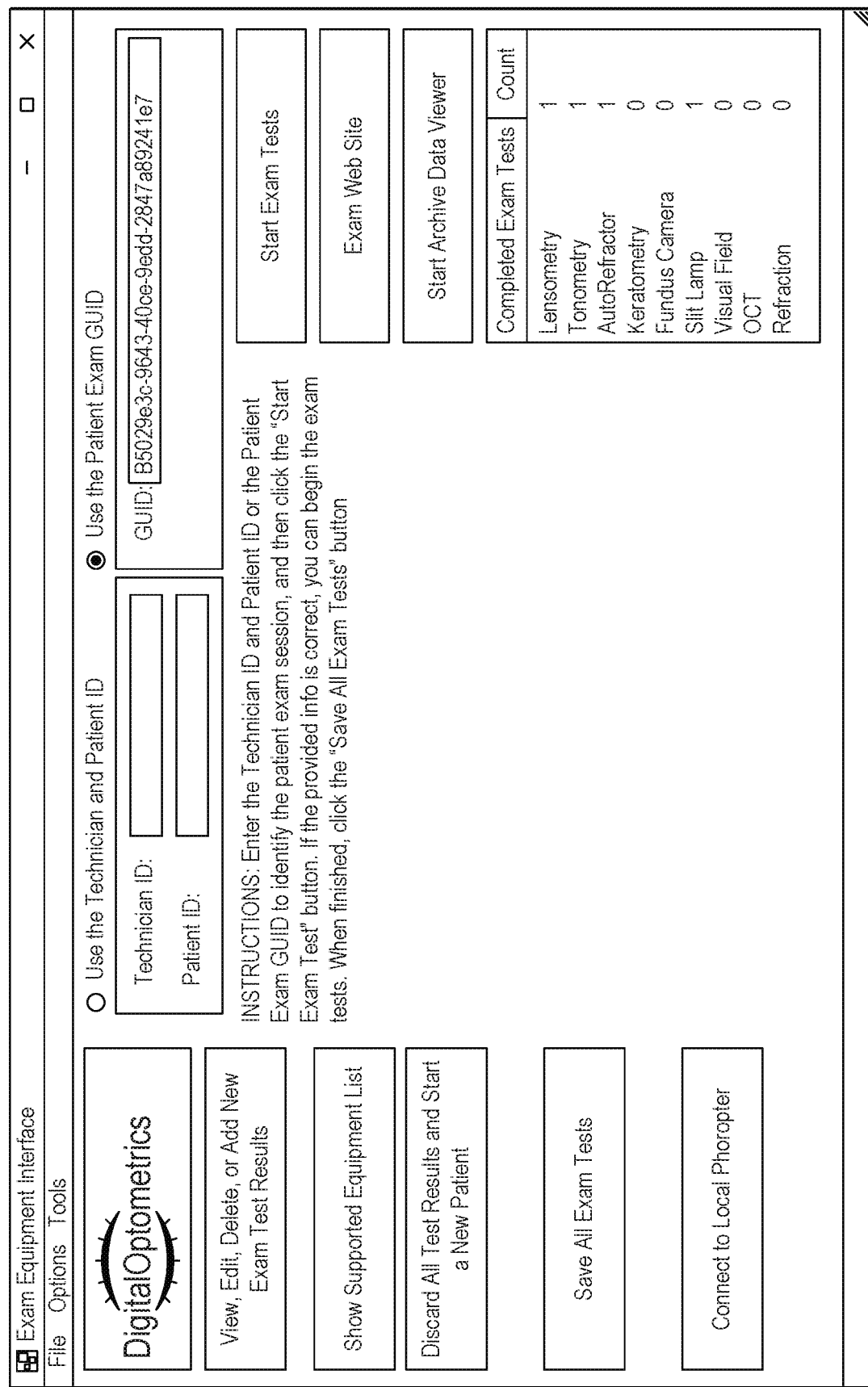
FIG. 3 is a machine interface screen for remote comprehensive eye examinations, in accordance with some embodiments.

An example of the machine interface screen is shown in FIG. 3.

Step 6: Submitting Exam Test Data 2006. The machine interface should now be minimized by clicking the—or X buttons on the top right corner of the main machine interface menu and the local technician's browser window should reappear. The exam tests the local technician just saved in the machine interface should show up in the "Completed Exam Tests" list within 60 seconds. Alternatively, the local technician can click the browser "Refresh" button to force the list to update itself immediately. The local technician can go back and repeat step 5 again if they need to perform additional tests for some reason. When the local technician has finished all local exam tests and is satisfied the results of all tests were transferred properly to the web site, the local technician will click the "Submit" button at the bottom of the local technician observation page.

Pinhole Visual Acuity: The local technician will typically begin the pre-refraction test by performing a pinhole visual acuity test on each eye. If the visual acuity results during this test indicate an issue with the patient's vision that cannot be corrected with a subjective refraction, the local technician will typically terminate the eye examination with a referral to a local doctor.

Step 7: Patient Waiting on Remote Technician 2007. After successfully completing the prior step, the patient will be automatically moved to the "Patient Waiting for Remote Technician" list. At this point during the patient's exam process, the local technician can do the following as it relates to a specific patient:

The video conference and subjective refraction "Session" with the remote technician can be started (if a remote technician has selected the patient).

The exam tests done up to this point can be viewed or optionally printed.

The exam can be terminated (the local technician will be required to provide a reason for the termination)

The patient can be reassigned to a different remote technician and/or remote doctor. When the "Start Session" button appears for a specific patient, this means a remote technician has selected the patient and is ready to begin a video conference and perform the subjective refraction. The local technician should position the patient properly behind the Phoropter and click the "Start Session" button when the button appears. This will begin the session with the remote technician.

Step 8: Video Conference and Remote Refraction 2008. The video conference window will now appear in the local technician's browser. The local technician will selected the specific webcam they want to use from the drop-down list and then they will click the button to start the video conference. If the remote technician has their video enabled, a live image will appear on the local technician's screen. If the remote technician has not enabled their video, the conference will be audio only. Either way, the remote technician, local technician, and patient will interact with one another as though they were located in the same room. The web site may popup a message asking for permission to use the local technician's camera and microphone. The local technician must select "Allow" or the video conferencing with the remote technician will not work. At this point the local technician must click the "Allow Phoropter Connection" button which will allow the remote technician to connect to the phoropter in the exam room and then the remote subjective refraction will begin. The refraction will include the same procedures and tests that are typically used during a non-remote subjective refraction.

(Section III.C titled "Remote Technician" has further detail about the remote technician's role in this part of the process.)

When the remote technician has finished the refraction, the video conference will end and the patient will be automatically moved to the "Patient Waiting for Remote Doctor" list.

Step 9: Patient Waiting on Remote Doctor 2009. After successfully completing the prior step, the patient will be automatically moved to the "Patient Waiting on Remote Doctor" list. At this point during the patient's exam process, the local technician can do the following as it relates to a specific patient:

- The video conference and optional subjective refraction "Session" with the remote doctor can be started (If a remote doctor has selected the patient).
- The exam tests done up to this point can be viewed or optionally printed.
- The exam can be terminated (the local technician will be required to provide a reason for the termination)
- The patient can be reassigned to a different remote doctor.

When the "Start Session" button appears for a specific patient, this means a remote doctor has selected the patient and is ready to begin a video conference and begin the doctor evaluation. The local technician should position the patient properly behind the phoropter in case the doctor wants to verify or refine the remote technician's subjective refraction. The local technician should then click the "Start Session" button when the button appears. This will begin the session with the remote doctor.

Step 10: Video Conference and Optional Remote Refraction 2010. The video conference window will now appear in the local technician's browser. The local technician will select the specific webcam they want to use from the drop-down list and then they will click the button to start the video conference. If the remote doctor has their video enabled, a live image will appear on the local technician's screen. If the remote doctor has not enabled their video, the conference will be audio only. Either way, the remote doctor, local technician, and patient will interact with one another as though they were located in the same room.

The web site may popup a message asking for permission to use the local technician's camera and microphone. The local technician must select "Allow" or the video conferencing with the remote doctor will not work.

At this point the doctor's evaluation of all exam test data collected up to this point will begin. The doctor may optionally choose to verify or refine the power of the subjective refraction done by the remote technician. The refraction will include the same procedures and tests that are typically used during a non-remote subjective refraction. The remote doctor will instruct the local technician to click the "Allow phoropter Connection" button (shown on the screen above) if the remote doctor decides to connect to the exam room phoropter and verify or refine the refraction.

(Section IV.D titled "Remote Doctor" has further detail about the remote doctor's role in this part of the process.)

When the remote doctor has completed the evaluation, the video conference will end and the patient will be automatically moved to the "Patient Waiting for Rx Print" list.

Step 11: Patient Waiting for Rx Print 2011. Patients who appear in this list have already completed their eye examination and new eyeglass and optional contact lens prescriptions have been authorized by the remote doctor. If the patient wants a copy of their prescription emailed, the local technician should click the "Email Prescription" button first and then click the "Print Prescription" button last. The prescription(s) will contain complete information you would typically find on a non-remote eye examination prescription along with the examining doctor's signature.

Step 12: Eye Exam Completed 2012. When the local technician has completed the previous step by printing a copy of the patient's prescription(s), the patient is automatically removed from all waiting lists and their eye exam is finished.

If the local technician, remote technician, or remote doctor terminates a patient's eye exam at any point before the prescription is issued, the patient will be moved directly into the "Patient Terminated Exams" list which is the very last list shown on the local technician dashboard.

If the local technician views or prints the "prescription" for a terminated exam, it will contain the reason the exam was terminated and the person's name who terminated the exam. This list is cleared each day, so it will only include patients who were terminated during the current day.

2. Maintenance Operations

The various maintenance operations that can be performed by the local technician after they login are described below.

Local technician dashboard. The local technician dashboard displays a list of patients currently waiting for the next stage of their eye exam. This allows the local technician to see at a glance the status of every patient who is waiting. The local technician login does not have an inactive timeout, so they will not be logged out of the web site for inactivity.

This local technician dashboard allows the local technician to perform the following tasks:

- The local technician can view a list of all patients at the exam site who are currently waiting to be seen by the local technician who is logged into the system. The patients in this list will appear in order of how long they have been waiting for a local technician with those who have been waiting the longest appearing at the top of the list.
- The local technician can view a list of all patients at the exam site who are currently waiting to be seen by a remote technician to have their subjective refraction performed. The patients in this list will appear in order of how long they have been waiting for a remote technician with those waiting the longest appearing at the top of the list. This list will also indicate if the patient is still waiting for a remote technician or if they are already in an active session with a remote technician.
- The local technician can view a list of all patients at the exam site who are currently waiting to have the results of all the exam and refraction tests reviewed by a remote doctor. The patients in this list will appear in order of how long they have been waiting for a remote doctor with those waiting the longest appearing at the top of the list. This list will also indicate if the patient is still waiting for a remote doctor or if they are already in an active session with a remote doctor.

The local technician dashboard provides the local technician with a good overview of what is going on in their specific exam site location as it involves them. The local technician does not have an inactive timeout, so a local technician can stay logged in 24 hours a day without any worry of being logged out.

Check Availability. The Check Availability menu option allows the local technician to start the exam process for a patient who is already registered in the system. Much more detail about the use of this menu option is included in step 2 of the "Eye Examination" section of this document.

Manage Patients. The local technician can use this menu option to perform the following tasks:
  Add a new patient to this exam site
  Edit the detail for an existing patient
  Manage documents for an existing patient (scans of medical records, insurance cards, driver's license, etc.)
  View the details for an existing patient
  View and optionally print the current and past exam results and prescriptions for a patient
  Email a copy of a prescription to a patient
  The patient is required to agree to the terms and the patient's signature is also required.

View Report. This menu option allows the local technician to do the following tasks:
  Select the desired report type from the list of reports available to local technicians
  Select the date range for the report
  Submit the choices to create the report
  View the resulting report
  Print the resulting report
  Export the resulting report
  Search within the report
  Reports available to the local technician will vary as additional reports are added by the system administrator.

Update Profile. The update profile menu option allows the local technician to view and update their profile details.

Information. This menu option will display a list of subjects available through internet links made available and assigned by system administrators. The subjects will typically be for training purposes, but the subject of the internet links made available through this menu option will be appropriate for local technicians and will be controlled remotely by system administrators and can be changed remotely at any time.

Change Password. This menu option simply allows the local technician to change their login password. The "Change Password" option requires the local technician to enter their old password, enter the new password, and confirm the new password. Certain requirements must be met on the complexity of the new password or the change will not be allowed.

After the local technician has successfully changed their password, they must log back in using the new password before they can continue using the system.

C. Remote Technician

The remote technicians in the system are responsible for performing the subjective refraction part of the eye exam prior to the patient being transferred to the remote doctor. The phoropter equipment and eye chart used for the subjective eye exam is controlled remotely by the remote technician using special controller software running at the remote technician's location.

A video conference session is established between the remote technician, the patient, and the local technician during the subjective refraction. This allows the remote technician, local technician, and patient to interact with each other during the subjective refraction in the same way they would interact if the refraction was being performed locally. This interaction combined with the special digital refraction equipment allows the remote technician to perform an extremely accurate subjective refraction and accurately check and record the patient's visual acuity.

The remote technician is allowed to review the lensometry, auto-refractor, and any subjective refraction test results that may have been previously performed during each exam session. The remote technician is not allowed to see the results of any other exam tests because the remaining tests must be evaluated by a remote doctor.

After the remote technician has completed all subjective refraction tests, the subjective refraction test results are reviewed by a remote doctor. The remote doctor can verify and even adjust the subjective refraction test results if they so desire by using the video conference system and controlling the phoropter exactly the same way as the remote technician.

If the remote technician is unable to recall their login password or username, they can use the "Forgot Password?" or "Forgot Username?" recovery options. Both recovery options will email the recovery instructions to the remote technician's email address. If the remote technician is unable to recall the email address that was used when their account was created, they will not be able to use these recovery options. In that case, they must contact the system administrator.

The remote technician directly participates in the patient's eye examination, but they also have a few maintenance operations they can perform as needed.

1. Eye Examination Operations

Figure 4:
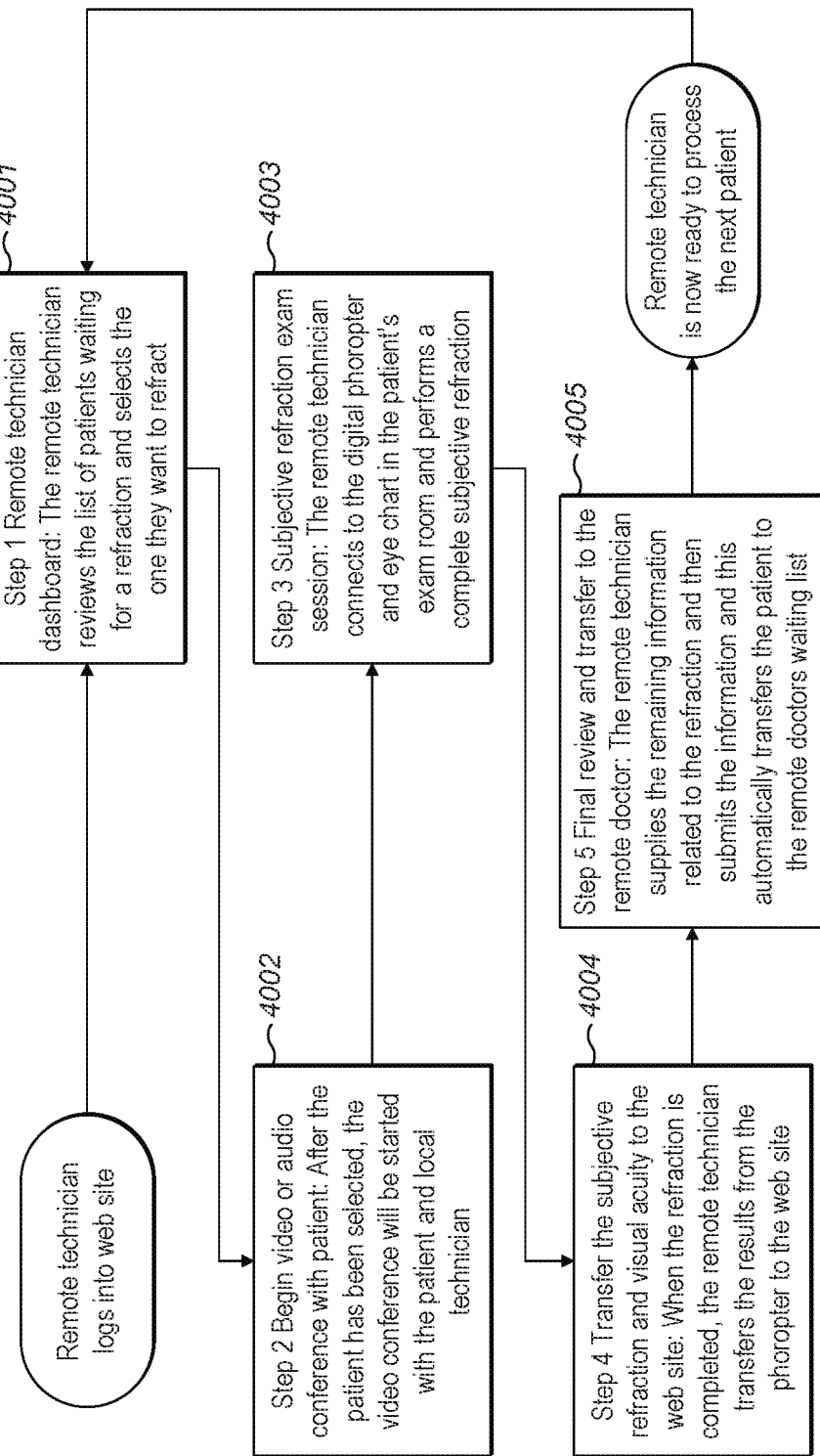
FIG. 4 is a flowchart showing the workflow of a remote technician for remote comprehensive eye examinations, in accordance with some embodiments.

As shown in FIG. 4, the various subjective refraction related eye examination operations that are performed by the remote technician after they login are described below.

Step 1: Remote Technician Dashboard 4001. The remote technician dashboard provides the remote technician the ability to get a good overview of everything in the system that will involve the specific remote technician who is logged in. The remote technician login has a 30 minute timeout, so they will be logged out of the system automatically if they have not performed any operations within the last 30 minutes.

This remote technician dashboard allows the remote technician to perform the following tasks:
  The remote technician can view a list of all patients currently waiting to have their subjective refraction performed. This list will contain patients waiting for any remote technician and patients waiting for this specific technician. Patients who are waiting for a different remote technician will not appear in this list. The patients in this list will appear in order of how long they have been waiting with those waiting the longest appearing at the top of the list.
  The remote technician can view a waiting patient's previous lensometry, auto-refractor, or refraction test results.
  The remote technician can terminate an eye examination for any reason. If the remote technician terminates an eye examination, they are required to enter the reason they terminated the exam.
  The remote technician can start the subjective refraction session. When the session begins, the remote technician will begin a video conference with the patient and begin the subjective refraction by remotely controlling the phoropter.

Step 2: Begin Video and/or Audio Conference with Patient 4002. When the remote technician clicks the "Session" button, the remote technician should then select the webcam they want to use for the video conference with the local technician and patient from the drop down list. After the correct webcam is selected, they should then click the icon to send a signal to the local technician that the remote technician is ready to begin the refraction. The video conferencing system allows the remote technician to communicate and interact with the patient and local technician as though they were in the same room.

The web site may popup a message asking for permission to use the remote technician's camera and microphone. The remote technician must select "Allow" or the video conferencing with the patient and local technician will not work.

Step 3: Subjective Refraction Exam Session 4003. After the video conference session has been established, the remote technician will then click a button on the web page to connect to the phoropter in the exam lane where the patient is located. At the same time, the local technician will use a button on their web page to allow the connection. Security implemented in this system makes it impossible for a remote technician to connect to the wrong phoropter. Once the controller/phoropter/eyechart connection has been established, the remote technician will have control of the phoropter and the eyechart and can begin the refraction. The digital equipment being used in this system allows the remote technician to perform a complete subjective refraction and related tests that will be at least as accurate as performing these tests locally. The remote technician will observe all precautions and "best practice" techniques as would be used for a typical non-remote subjective refraction.

Normal Visual Acuity: The remote technician will check the patient's visual acuity for each eye and then for both eyes together under the following conditions:
  With no correction for the right and left eye
  With no correction for both eyes together
  With their previous prescription for the right and left eye
  With their previous prescription for both eyes together Subjective Distance Vision Refraction: The remote technician will remotely control the phoropter and eye chart to perform a distance vision subjective refraction on each eye. The subjective refraction tests performed for distance vision will be the same as the tests normally performed during a non-remote subjective eye examination. The steps will typically include the following and in the following order:
  Refine the right eye sphere power
  Refine the right eye cylinder axis
  Refine the right eye cylinder power
  Refine the right sphere power one last time
  Refine the left eye sphere power
  Refine the left eye cylinder axis
  Refine the left eye cylinder power
  Refine the left sphere power one last time
  Refine the right eye sphere using the Red/Green duochrome test
  Refine the left eye sphere using the Red/Green duochrome test
  Perform the binocular balance tests with both eyes together Subjective Near Vision Refraction: The remote technician will remotely control the phoropter and eye chart to perform a typical near vision refraction if the patient is beyond a certain age or if the patient indicates they are having difficulty seeing at close distances or reading. The subjective refraction tests performed for near vision will be the same as the tests typically performed during a non-remote subjective eye examination.

Figure 5:
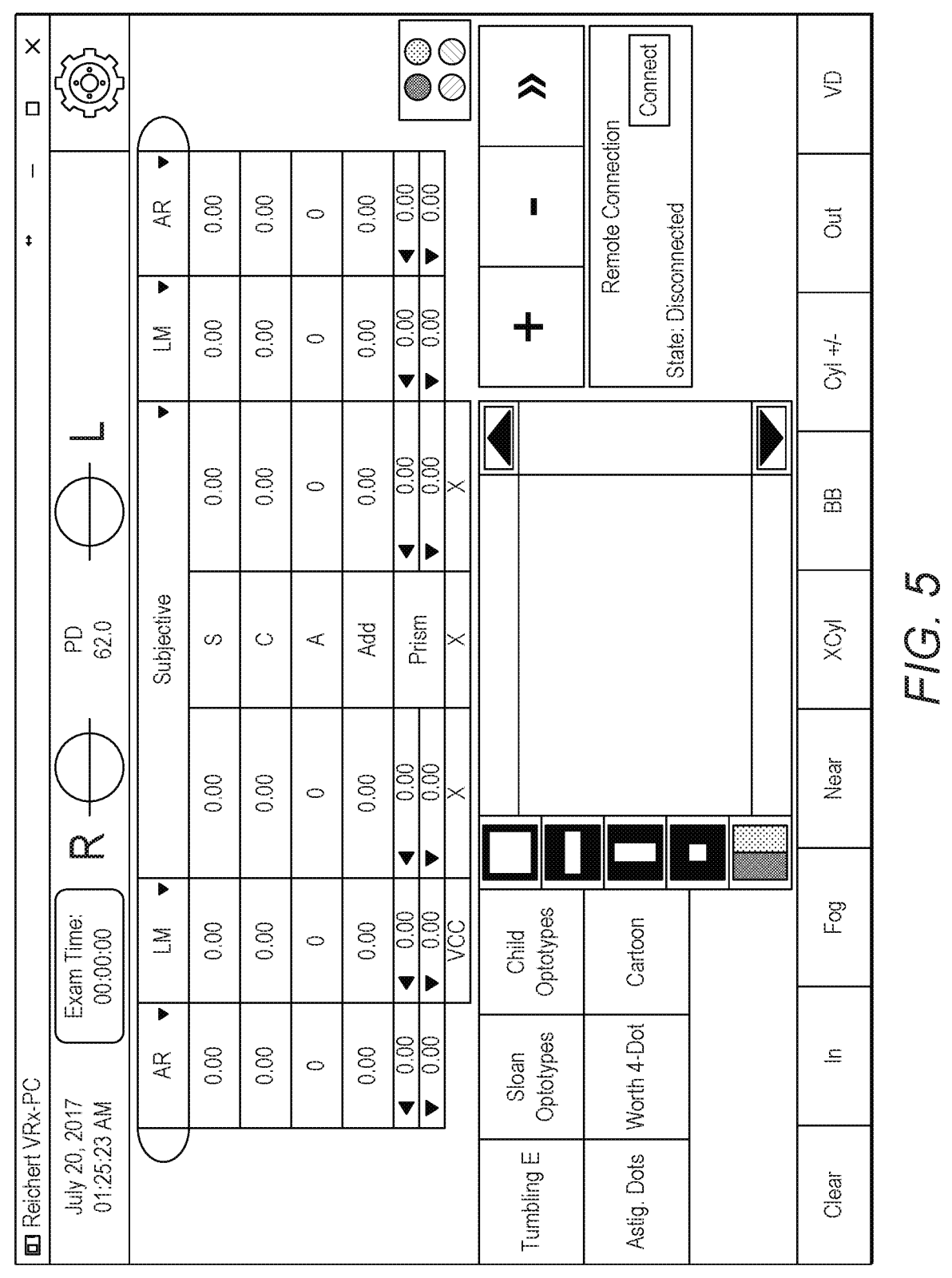

Final Visual Acuity: The remote technician will now use the eye chart to perform the final visual acuity check for distance and near with the new prescription and save all test results.
  New distance vision visual acuity for the right eye
  New distance vision visual acuity for the left eye
  New distance vision visual acuity with both eyes together
  New near vision visual acuity for the right eye
  New near vision visual acuity for the left eye
  New near vision visual acuity with both eyes together The phoropter and eye chart controller is not necessarily the property of the system so the appearance and functionality of the controller will vary from one equipment manufacturer to another. An example of the controller menu that is used by the remote technician to remotely control a Reichert VRx phoropter and eye chart during the subjective refraction is shown in FIG. 5.

Step 4: Transfer the Subjective Refraction and Visual Acuity Test Results to the Web Site 4004: When the remote technician has completed all subjective refraction tests, the results of all tests are sent from the phoropter to the machine interface at the exam site, and then on to the web site. The remote technician will then click the "Get Refraction Data" button and the newest refraction done during the current exam session will be loaded into the form. The remote technician can then choose the type of lens the patient requests or that is indicated by the patient's required lens power. The remote technician may also choose to add comments for the remote doctor who will be doing the final evaluation.

Step 5: Final Review and Transfer to the Remote Doctor 4005: When the remote technician is satisfied all important information has been added, they will click the submit button. The web site will verify everything is valid and will then take the remote technician back to the remote technician dashboard and remove the patient from the patient waiting list. At this point, the patient will be moved into the remote doctor's waiting list.

2. Maintenance Operations

The various maintenance operations that can be performed by the remote technician after they login are described below.

Remote Technician Dashboard. The remote technician dashboard provides the remote technician the ability to see a list of patients who are waiting for refractions. Details about the remote technician dashboard are included in the previous "Eye Exam Operations" section of this document.

View Report. This menu option allows the remote technician to do the following tasks:
  Select the desired report type from the list of reports available to remote technicians
  Select the date range for the report
  Submit the choices to create the report
  View the resulting report
  Print the resulting report
  Export the resulting report
  Search within the report Reports available to the remote technicians will vary as additional reports are added by the system administrator.

Update Profile. The update profile menu option allows the remote technician to view and update their profile details Information. This menu option will display a list of subjects available through internet links made available and assigned by system administrators. The subjects will typically be for training purposes and appropriate for remote technicians. The subject of the internet links made available through this menu option is controlled remotely by system administrators and can be changed remotely at any time.

Change Password. This menu option allows the remote technician to change their login password. The "Change Password" option requires the remote technician to enter their old password, enter the new password, and confirm the new password. Certain requirements must be met on the complexity of the new password or the change will not be allowed. After the remote technician has successfully changed their password, they must log back in using the new password before they can continue using the system.

D. Remote Doctor

The remote doctors in the system are responsible for evaluating the results of all tests performed during the eye examination process and they may optionally verify or refine the subjective refraction performed by the remote technician. The phoropter equipment and eye chart used for the subjective eye exam can be controlled remotely by the remote doctor using special controller software running at the remote doctor's location.

A video conference session is established between the remote doctor, the patient, and the local technician during the doctor's evaluation session. This allows the remote doctor, patient, and local technician to interact with each other in the same way they would interact if the doctor's evaluation was being performed locally. This interaction combined with the use of the most modern examination equipment allows the remote doctor to perform an extremely thorough evaluation that is at least as accurate as a non-remote doctor evaluation.

The remote doctor is required to review the results of all exam tests that have been previously performed during each exam session including any media files that may be attached to any exam test. The doctor is also allowed to review all patient history information and any information collected during any previous eye exam that is on file. The remote doctor is also allowed to verify or refine any subjective refraction previously performed during this exam session.

After the remote doctor has reviewed everything, they may issue a prescription for eyeglasses, optionally issue a prescription for contact lenses, or they may choose to terminate the eye exam. The doctor will not issue a contact lens prescription unless the patient has requested contact lenses and all contact lens related tests and fitting operations have been successfully performed.

If the remote doctor is unable to recall their login password or username, they can use the "Forgot Password?" or "Forgot Username?" recovery options. Both recovery options will email the recovery instructions to the remote doctor's email address. If the remote doctor is unable to recall the email address that was used when their account was created, they will not be able to use these recovery options. In that case, they must contact the system administrator.

The remote doctor directly participates in the final steps of the patient's eye examination and makes the final decisions, but they also have a few maintenance operations they can perform as needed.

1. Eye Examination Operations

Figure 6:
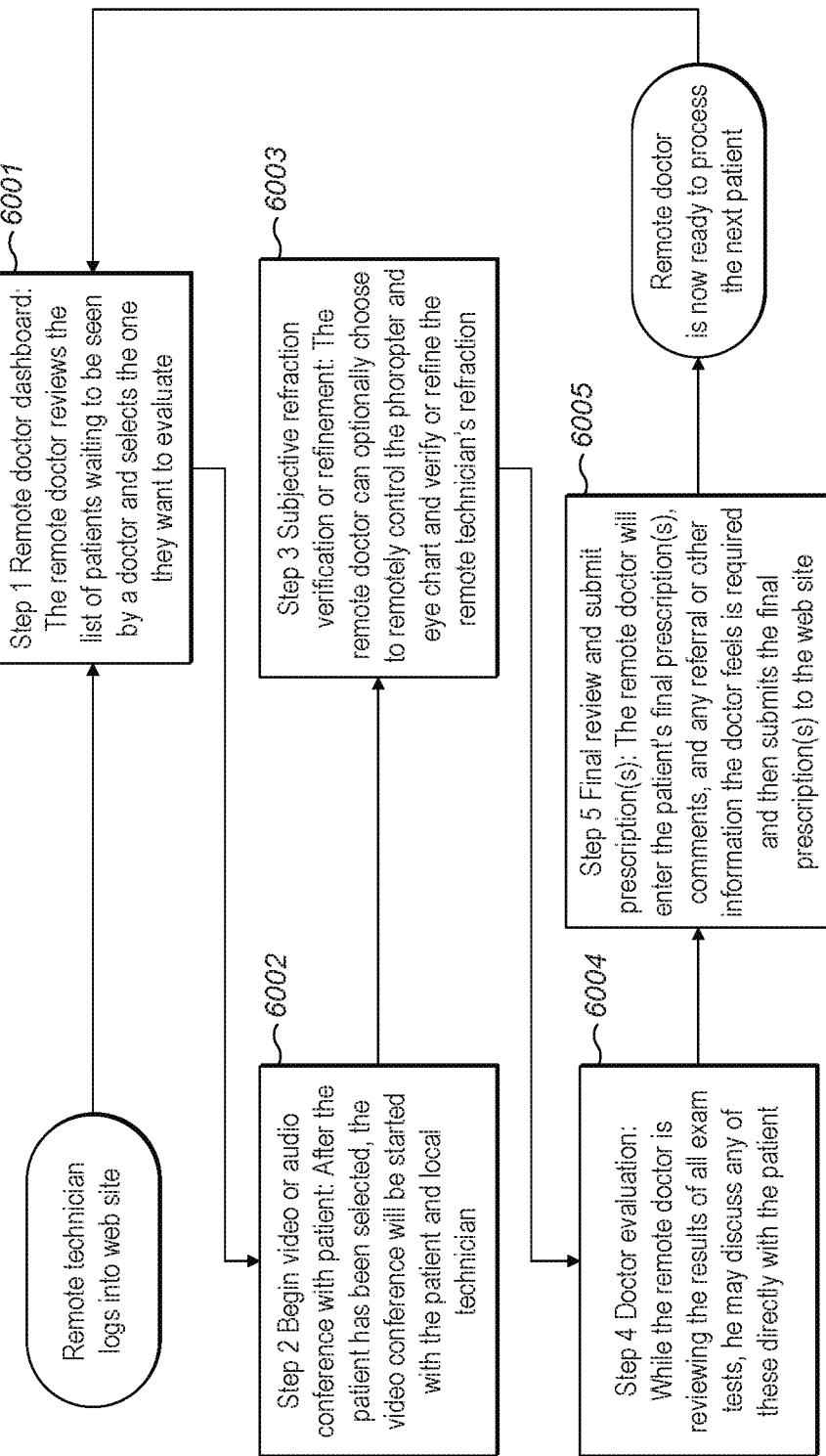
FIG. 6 is a flowchart showing the workflow of a remote doctor for remote comprehensive eye examinations, in accordance with some embodiments.

As shown in FIG. 6, the various evaluation and subjective refraction related operations that can be performed by the remote doctor after they login are described below.

Step 1: Remote Doctor Dashboard 6001. The remote doctor dashboard provides a good overview of everything in the system that will involve the specific remote doctor who is logged in. The remote doctor login has a 30 minute timeout, so they will be logged out of the system automatically if they have not performed any operations within the last 30 minutes.

This remote doctor dashboard allows the remote doctor to perform the following tasks:

The remote doctor can view a list of all patients currently waiting to have their eye exam tests evaluated and their eyeglass and optionally contact lens prescriptions issued. This list will contain patients waiting for any remote doctor and patients waiting for the specific doctor who is logged in. Patients who are waiting for a different remote doctor will not appear in this list. The patients in this list will appear in order of how long they have been waiting with those waiting the longest appearing at the top of the list.

The remote doctor can see the group and exam site name and address where each patient is physically located.

The remote doctor can view the results of all tests performed for any waiting patient.

The remote doctor can terminate an eye examination for any reason. If the remote doctor terminates an eye examination, they are required to enter the reason they terminated the exam.

The remote doctor can start the eye exam evaluation session. When the session begins, the remote doctor will typically begin a video conference with the patient, begin evaluating the test results, and optionally control the phoropter remotely if they want to verify or refine the subjective refraction results.

Step 2: Begin Video and/or Audio Conference with Patient 6002. When the remote doctor clicks the "Add Prescription" button as shown on the doctor's dashboard above, the webcam and prescription web pages will display. The remote doctor should then select the webcam they want to use for the video conference with the local technician and patient from the drop down list. After the correct webcam is selected, they should then click the icon to send a signal to the local technician that the remote doctor is ready to see the patient and begin the evaluation session.

The web site may popup a message asking for permission to use the remote doctor's camera and microphone. The remote doctor must select "Allow" or the video conferencing with the patient and local technician will not work. The video conferencing system allows the remote doctor to communicate and interact with the patient and local technician as though they were in the same room.

Step 3: Optional Subjective Refraction Verification or Refinement 6003. After the video conference session has been established, the remote doctor can optionally verify or refine the refraction done by the remote technician. A button on the web page allows them to connect to the phoropter in the exam lane where the patient is located. At the same time, the remote doctor will use a button on their web page to allow the phoropter connection. Security implemented in this system makes it impossible for a remote doctor to connect to the wrong phoropter. Once the controller/phoropter/eyechart connection has been established, the remote doctor will have control of the phoropter and the eyechart and can begin the refraction verification or refinement. The digital equipment being used in this system allows the remote doctor to perform a subjective refraction and related tests that will be at least as accurate as performing these tests locally. The remote doctor will observe all precautions and "best practice" techniques as would be used for typical a non-remote subjective refraction if they do choose to verify or refine the refraction during their evaluation.

The phoropter and eye chart controller is not the property of the system so the appearance and functionality of the controller will vary from one equipment manufacturer to another. An example of the controller menu that may be used by the remote doctor to remotely control a Reichert VRx phoropter and eye chart is shown in FIG. 5. Another model of a phoropter may also be used.

Step 4: Doctor Evaluation 6004. The video conference will continue while the remote doctor is reviewing all exam test results for the current patient. The doctor may choose to carry on a conversation with the patient while the test results are being examined. The web site will NOT allow the doctor to issue a prescription until they have reviewed the results of every exam test, all attached media files, and the patient's visual and medical history information. This system behavior assures that the remote doctor will review everything available, which makes the system significantly more thorough than a typical non-remote eye examination.

During the comprehensive eye exam, images of the patient's eyes are typically collected by various eye exam devices such as a fundus camera. The remote eye exam system contains a feature that allows the remote eye doctor to remotely display any or all images of the eye to the patient that were produced during the eye exam. This is typically done during the remote doctor's video/audio conference with the patient. This allows the doctor to verbally explain things of interest or concern that may be found in any or all of the eye exam images while the patient is looking at the actual image. This feature also allows the remote doctor to remotely highlight areas of interest on any of the eye exam images using circles, lines, squares, text or freehand drawing and all of these annotations appear on the image being displayed to the patient. This feature allows the remote doctor to be as detailed as needed when reviewing images produced during the patient's eye exam.

During the comprehensive eye exam, video recordings of the patient's eyes are typically collected by various eye exam devices such as a video slit lamp. The remote eye exam system contains a feature that allows the remote doctor to remotely display any or all videos of the eye to the patient that were produced during the eye exam. This is typically done during the remote doctor's video/audio conference with the patient. This allows the remote doctor to verbally explain things of interest or concern that may be found in any or all of the eye exam videos while the patient is watching the actual video. This feature allows the remote doctor to stop or pause the video at various points of interest to explain an image in the video in greater detail. This feature also allows the remote doctor to remotely highlight areas of interest on the video image using circles, lines, squares, text or freehand drawing and all of these annotations appear on the video being displayed to the patient. This feature allows the remote doctor to be as detailed as needed when reviewing videos produced during the patient's eye exam.

When the remote doctor has reviewed an exam test for the current exam session along with all media files attached to the exam test, the tab for that exam test will turn green. Exam test results that have not been fully reviewed will remain light blue.

In addition to the exam tests, the remote doctor is also required to review the patient's visual and medical history information before they are allowed to issue a prescription.

The remote doctor may choose to review information from prior eye exams, but they are not required to do so.

The remote doctor will click the "Copy Refraction to This Form" button when they are satisfied the most recent refraction done during today's eye exam is accurate and correct. This will automatically load the most recent refraction data into the remote doctor's prescription form.

If the patient requested contact lenses and adequate testing has been done to proceed with a contact lens exam, the doctor will place a check mark in the "Add Contact Lens Prescription" checkbox. The remote doctor may instruct the local technician through the video conferencing system to have the patient insert specific trial contact lenses and provide additional slit lamp images and/or video so the remote doctor can evaluate the fit. The doctor will repeat this process until the contact lens is correct.

Start Video Conferencing system: The remote doctor will typically begin the evaluation with the patient by starting a video conference session. This will allow the doctor to interact with the patient in the same way they would do in a non-remote eye exam.

Review Exam Test Results: The remote doctor will review all exam tests results and this will typically involve the following:

Mandatory: Review all exam tests performed by the local and remote technicians. This will include all tests that are normally performed during a typical non-remote eye examination.

Mandatory: Review all media files that may be attached to any exam test.

Mandatory: Review the patient's medical history.

Optional: Verify or refine the subjective refraction by the remote doctor's use of the phoropter remotely and applying professional judgement.

Optional: View the exam test results of any previous eye exam performed through this system.

Optional: View the patient history attached to any previous eye exam performed through this system.

Mandatory: Issue an eyeglass prescription or the doctor may choose to terminate the eye exam and provide a referral if necessary in their professional opinion. If the doctor terminates the exam, they MUST provide a reason and optionally provide a referral.

Optional: They may issue a contact lens prescription if the patient asks for contacts and all tests and fitting requirements for contact lenses have been successfully performed.

In addition, there may be times when the remote doctor observes something during the exam that requires a referral to a specialist. This would typically happen while the remote doctor is evaluating the results of the eye exam tests during the video conference with the patient. The remote comprehensive eye exam system contains an automatic doctor referral system allows the remote eye doctor to simply click a referral button during the patient's eye exam if a referral is required.

The referring doctor is able to choose from a list of referral doctors along with their location and the areas in which they specialize. The referring doctor will typically choose a referral doctor located near the exam site where the patient is located. They will also typically choose a referral doctor who specializes in the appropriate area of expertise that is of concern on that particular patient.

After the remote doctor has completed the eye exam, the system will automatically print a referral letter at the exam site to be given to the patient and/or sent to the referral doctor. It will optionally print the results from all exam tests along with all the remote doctor's notes that can be given to the patient, or sent directly to the referral doctor.

This feature saves the remote doctor considerable time compared to manually finding a referral doctor, preparing the referral letter, and preparing the exam data for the referral doctor. The ease of use of the automatic referral system also encourages the remote doctor to refer a patient anytime he/she sees anything of concern.

Step 5: Final Review and Submit Prescription(s) 6005. The remote doctor can now optionally attach comments to the final prescriptions before submitting them to the system. When the remote doctor is satisfied all important information has been added to the prescription(s), they will click the submit button. The web site will verify everything is valid and will then take the remote doctor back to the remote doctor dashboard and remove the patient from the patient waiting list.

The remote doctor is now ready to see the next patient that appears in their waiting list.

2. Maintenance Operations

The various maintenance operations that can be performed by the remote doctor after they login are described below.

Remote Doctor Dashboard. The remote doctor dashboard provides the remote doctor the ability to see a list of patients who are waiting for a doctor to see them and evaluate the test results and issue their prescription(s) Details about the remote doctor dashboard are included in the previous "Eye Examination Operations" section of this document.

View Report. This menu option allows the remote doctor to do the following tasks:
    Select the desired report type from the list of reports available to remote doctors
    Select the date range for the report
    Submit the choices to create the report
    View the resulting report
    Print the resulting report
    Export the resulting report
    Search within the report Reports available to the remote doctors will vary as additional reports are added by the system administrator.

Update Profile. The update profile menu option allows the remote doctor to view and update their profile details.

Information. This menu option will display a list of subjects available through internet links made available and assigned by system administrators. The subjects will typically be for training purposes and appropriate for remote doctors. The subject of the internet links made available through this menu option is controlled remotely by system administrators and can be changed remotely at any time.

Change Password. This menu option allows the remote doctor to change their login password. The "Change Password" option requires the remote doctor to enter their old password, enter the new password, and confirm the new password. Certain requirements must be met on the complexity of the new password or the change will not be allowed. After the remote doctor has successfully changed their password, they must log back in using the new password before they can continue using the system.

V. Maintenance Operations

The following provides a comprehensive description of role of each participant in the maintenance of the apparatus, method, and system for remote comprehensive eye examinations: the system administrator, the group administrator and the exam site administrator.

A. System Administrator

1. Overview

The system administrator users oversee the entire system. They can create new groups, exam sites, remote technicians, remote doctors, and supported insurances as needed and perform other system maintenance activities. The system administrators will typically be high level managers.

If a system administrator is unable to recall their login password or username, they can use the "Forgot Password?" or "Forgot Username?" recovery options. Both recovery options will email the recovery instructions to the system administrator's email address. The system administrator does not directly participate in a patient's eye examination. The role of the system administrator is primarily to observe the activity going on within the system and to maintain and manage the groups, exam sites, remote technicians and remote doctors.

2. Operations

The various system maintenance operations that can be performed by the system administrator after they login are described below.

Manage Administrators. The system administrator uses this menu option to manage the system administrators in the system. This menu option allows the system administrator to perform the following tasks:
    Add system administrators into the system
    Add, edit, delete, and manage documents for system administrators that are currently in the system (only available to administrators with "Super" status)
    View detail about system administrators currently in the system
    Maintain documents for any group or any exam site within any group Manage Groups. The system administrator uses this menu option to manage the groups in the system. This menu option allows the system administrator to perform the following tasks:
    Add new groups into the system
    Delete groups that are currently in the system
    Add, delete, view, or edit exam sites for any group currently in the system
    View or edit the exam pricing currently assigned to any group
    View or Edit the exam pricing currently assigned to any exam site in any group
    Maintain documents for any group or any exam site within any group
    View the detail for any group currently in the system Manage Local Technicians. The system administrator can manage the local technicians who are allowed to perform pre-refraction tests at each of the group's exam sites. This menu option allows the system administrator to perform the following tasks:
    Add a new local technician to any existing group
    Edit the details for an existing local technician in any group.
    Delete an existing local technician that is in any group
    View the detail for an existing local technician in any group
    Specify the exam site where each local technician is allowed to perform their work
    Manage and view Documents for an existing local technician in any group Manage Remote Technicians. The system administrator can this menu option to perform the following tasks:
    Add a new remote technician to the system
    Edit the details for an existing remote technician
    Delete an existing remote technician
    View the detail for an existing remote technician
    Specify the exam site where each remote technician is allowed to perform their work
    Manage and view Documents for an existing remote technician Manage Patients. This menu option allows the system administrator to do the following tasks:
    Search and View a list of patients currently in the system
    Delete a patient from the system The primary use of this menu option is to remove old patient records or experimental records that no longer need to be in the system.

View Report. This menu option allows the system administrator to do the following tasks:
- Select the desired report type from the list of reports available to the main system administrators
- Select the date range for the report
- Submit the choices to create the report
- View the resulting report
- Print the resulting report
- Export the resulting report
- Search within the report Reports available to the system administrator will vary as additional reports are added by the system administrator.

Manage Doctors. The system administrator can use this menu option to perform the following tasks:
- Add a new doctor to the system
- Edit the details for an existing doctor
- Delete an existing doctor
- View the detail for an existing doctor
- Specify the exam site where each doctor is allowed to perform their work
- Manage and view documents for an existing doctor Manage Insurances. The system administrator uses this menu option to perform the following tasks:
- Add a new insurance program to the system
- Edit the details for an existing insurance program
- Delete an existing insurance program
- View the detail for an existing insurance program
- Manage and view documents for an existing insurance program Manage Report. This menu option allows the system administrator to create new reports and edit existing reports. The system administrator can specify what login type is able to view each report.

Manage Pricing. This menu option is a utility that allows the system administrator to change the prices on large numbers of groups and exam sites at once.

Patient Waiting List. This menu option allows the system administrator to see a list of patients currently waiting to be seen at all exam sites. The primary purpose of this option is to allow a system administrator to observe the patient waiting times and possibly take action if an excessive waiting time is observed on any patient.

Manage Patient Portal. This menu option allows the system administrator to enter, edit, or delete the internet links and link descriptions that will be available to patients who visit any exam site in the system when they sign into their patient portal. These links are used for patient education and for entertainment purposes, such as news, weather, or sports information. This feature allows the system administrator to assign custom links for entertainment or education in addition to providing information about the eye exam process itself and how it works. The purpose of this feature is to significantly enhance the patient experience by incorporating patient portal tablets into the exam process.

If a patient signs into the patient portal using the patient portal kiosk, the patient will be presented with a menu option that will allow them to visit only the web sites specified by the main system administrator, the group administrator, and the exam site administrator. The same educational and entertainment links will be available if they sign into the patient portal from their home or work computer, but their browser will not be restricted as to where it can go.

Update Profile. This menu option allows the logged in system administrator to update their own profile information.

Change Password. This menu option allows the system administrator to change their login password. The "Change Password" option requires the system administrator to enter their old password, enter the new password, and confirm the new password. Certain requirements must be met on the complexity of the new password or the change will not be allowed. After the system administrator has successfully changed their password, they must log back in using the new password before they can continue using the system.

Doctor Networks. Some optical exam sites have their own doctors on staff. When their doctors are signed into the remote eye exam system and are available, the local technicians at the exam site will typically select one of their own doctors ("In Network") to perform the remote eye exams. When there are no "In Network" doctors available at the time an exam site requires a doctor to perform a remote eye exam, the local technician at that exam site will have to choose a doctor not on staff ("Out of Network") to perform the optical exam on the patient. Doctors may be assigned as both "In Network" and "Out of Network" doctors and the system has the capability to handle these "In Network" and "Out of Network" exam situations.

B. Group Administrator

1. Overview

The group administrator users in the system oversee the exam sites within their group. They can create new exam sites/stores within their group as needed and perform other maintenance activities. A chain store operation for example would have many exam sites within their group, whereas an independent operation may only have one exam site in their group.

If the group administrator is unable to recall their login password or username, they can use the "Forgot Password?" or "Forgot Username?" recovery options. Both recovery options will email the recovery instructions to the group administrator's email address. If the group administrator is unable to recall the email address that was used when their account was created, they will not be able to use these recovery options. In that case, they must contact the system administrator.

The group administrator does not directly participate in a patient's eye examination. The role of the group administrator is primarily to observe the activity going on within their group and to maintain the exam sites and local technicians who are part of their group.

2. Operations

The various system maintenance operations that can be performed by the group administrator after they login is described below.

Group Dashboard. The group administrator can view the group dashboard. This menu option allows the group administrator to perform the following tasks:
- View a list of all local technicians currently registered to perform pre-refraction exam tests for exam sites in their group
- View a list of all remote technicians who are able to perform refractions for the exam sites in their group
- View a list of remote doctors who are able to evaluate patient exam tests, refraction results, and sign prescriptions for the various exam sites within that group
- View a list of all patients who are currently engaged in an eye exam at an exam site within their group The group dashboard provides the group administrator the ability to get a good overview of what is going on within their entire group. The group administrator login does not have an inactive timeout, so a monitor can display the group dashboard detail at the group's corporate office 24 hours a day without any worry of being logged out.

Manage Local Technicians. The group administrator can manage the local technicians who are allowed to perform pre-refraction tests at each of the group's exam sites. This menu option allows the group administrator to perform the following tasks:
- Add a new local technician to the group
- Edit the details for an existing local technician in the group.
- Delete an existing local technician that is in the group
- View the detail for an existing local technician in the group
- Specify the exam site where each local technician is allowed to perform their work
- Manage and view Documents for an existing local technician in the group Group Profile. The group profile menu option allows the group administrator to view the details about their group that has been stored in the system by the main system administrator. If any of this information needs to be updated, the group administrator must contact the system administrator.

Manage Exam Sites. The group administrator can use this menu option to perform the following tasks:
- Add a new exam site to the group
- Edit the detail for any exam site in the group
- Delete an exam site from the group
- View the exam pricing for any exam site in the group
- Maintain documents for any exam site in the group View Report. This menu option allows the group administrator to do the following tasks:
- Select the desired report type from the list of reports available to groups
- Select the date range for the report
- Submit the choices to create the report
- View the resulting report
- Print the resulting report
- Export the resulting report
- Search within the report Reports available to the group administrator will vary as additional reports are added by the system administrator.

View Pricing. This menu option allows the group administrator to view the exam pricing that is currently assigned by the system to this group. The prices displayed here for the various exam types will be used for any exam site in this group that does not have custom exam prices assigned by the system.

Manage Patient Portal. This menu option allows the group administrator to enter, edit, or delete the internet links and link descriptions that will be available to patients at one of their exam sites when they sign into their patient portal. These links are used for patient education and for entertainment purposes, such as news, weather, or sports information.

This feature allows the group administrator to assign custom links for education or entertainment that are more focused on the needs of the patients when they visit an exam site associated with their specific group. The purpose of this feature is to significantly enhance the patient experience by incorporating patient portal tablets into the exam process.

If a patient signs into the patient portal using the patient portal kiosk, the patient will be presented with a menu option that will allow them to visit only the web sites specified by the main system administrator, the group administrator, and the exam site administrator. The same educational and entertainment links will be available if they sign into the patient portal from their home or work computer, but their browser will not be restricted as to where it can go.

Information. This menu option will display a list of subjects available through internet links made available and assigned by system administrators. The subjects will typically be for training purposes and appropriate for group administrators. The subject of the internet links made available through this menu option is controlled remotely by system administrators and can be changed remotely at any time.

Change Password. This menu option allows the group administrator to change their login password. The "Change Password" option requires the group administrator to enter their old password, enter the new password, and confirm the new password. Certain requirements must be met on the complexity of the new password or the change will not be allowed. After the group administrator has successfully changed their password, they must log back in using the new password before they can continue using the system.

Preferred Products. The preferred products feature allows the group administrator to assign eyecare-related products (such as eyeglass and contact lens products) that their stores are allowed to sell. In turn, the administrator at each exam site within the group is then able to specify the items from the group's product list that they will sell and also specify which products they typically have in stock. The eyeglass and contacts lens products selected by the exam site administrator are then available for the remote doctor to choose from when the doctor is doing an eye exam for a patient at the exam site. This feature lets the remote doctor know which products are sold and stocked at each exam site. When prescribing eyeglass or contact lens, the remote doctor can choose products from the exam site's availability list, or they can choose to prescribed something the exam site does not sell if the doctor feels it would be in the best interest of the patient.

C. Exam Site Administrator

1. Overview

The exam site administrator in the system is the administrator for the individual exam sites. They can create new local technicians for their location as needed and perform other maintenance activities for their exam site. If the exam site administrator is unable to recall their login password or username, they can use the "Forgot Password?" or "Forgot Username?" recovery options as long as they still remember the exam site administrator's email address. The recovery options will email the recovery instructions to the exam site administrator's email address. If they are also unable to recall the email address, they must contact the system administrator.

The exam site administrator does not directly participate in a patient's eye examination. The role of the exam site administrator is primarily to observe the activity going on at their exam site and to maintain local technician information and occasionally patient information for their exam site.

2. Operations

The various system maintenance operations that can be performed by the exam site administrator after they login is described below.

Exam Site Dashboard. The exam site administrator can view the exam site dashboard. This menu option allows the exam site administrator to perform the following tasks:
- View a list of all patients at this exam site who are currently waiting on a local technician to start their pre-refraction exam tests View a list of all patients at this exam site who are currently waiting on a remote technician to begin their refraction View a list of all patients at this exam site who are currently waiting on a remote doctor to review their exam tests and refraction View a list of all patients at this exam site who have had their entire eye exam completed and are simply waiting to have their prescription printed and optionally emailed The exam site dashboard provides the exam site administrator with the ability to get a good overview of what is going on in their specific exam site location. The exam site administrator login does not have an inactive timeout, so a monitor can display the exam site dashboard detail in the back office at the exam site location 24 hours a day without any worry of being logged out.

Update Profile. The update profile menu option allows the exam site administrator to view the details about their exam site that has been stored in the system by the main system administrator. If any of this information needs to be updated, the exam site administrator must contact the system administrator.

Manage Patients. The exam site administrator can use this menu option to perform the following tasks:

Add a new patient to this exam site

Edit the detail for an existing patient

Manage documents for an existing patient (scans of medical records, insurance cards, driver's license, etc.)

View the details for an existing patient

View and optionally print the current and past exam results and prescriptions for a patient Email a copy of a prescription to a patient Manage Local Technicians. The exam site administrator can also manage the local technicians who are allowed to perform pre-refraction tests at this specific exam site. This menu option allows the exam site administrator to perform the following tasks:

Add new local technicians for this exam site

Edit detail for an existing local technician for this exam site

Delete a local technician from this exam site

Manage and view documents for an existing local technician (scanned certifications, licenses, etc.)

View the details for an existing local technician at this exam site

View Report. This menu option allows the exam site administrator to do the following tasks:

Select the desired report type from the list of reports available to exam site administrators Select the date range for the report Submit the choices to create the report View the resulting report Print the resulting report Export the resulting report Search within the report Reports available to the exam site administrator will vary as additional reports are added by the system administrator.

View Pricing. This menu option allows the exam site administrator to view the exam pricing that is currently assigned by the system to this exam site.

Manage Patient Portal. This menu option allows the exam site administrator to enter, edit, or delete the internet links and link descriptions that will be available to their patients when they sign into their patient portal. These links are used for patient education and for entertainment purposes, such as news, weather, or sports information.

This feature allows the exam site administrator to assign custom links for education or entertainment that are focused on the local needs of their specific patients. The purpose of this feature is to significantly enhance the patient experience by incorporating patient portal tablets into the exam process.

If a patient signs into the patient portal using the patient portal kiosk, the patient will be presented with a menu option that will allow them to visit only the web sites specified by the main system administrator, the group administrator, and the exam site administrator. The same educational and entertainment links will be available if they sign into the patient portal from their home or work computer, but their browser will not be restricted as to where it can go.

Information. This menu option will display a list of subjects available through internet links made available and assigned by system administrators. The subjects will typically be for training purposes and appropriate for exam site administrators. The subject of the internet links made available through this menu option is controlled remotely by system administrators and can be changed remotely at any time.

Change Password. This menu option simply allows the exam site administrator to change their login password. The "Change Password" option requires the exam site administrator to enter their old password, enter the new password, and confirm the new password. Certain requirements must be met on the complexity of the new password or the change will not be allowed. After the exam site administrator has successfully changed their password, they must log back in using the new password before they can continue using the system.

D. Voice-Activated Transcription

Many of the data entry fields used in the foregoing system that are open text fields have an optional transcription feature that allows the person doing the data entry to simply speak what they want to enter in a data field. The words of the person are transcribed into text and automatically entered in the selected field. This feature can save considerable time for example when the remote doctor needs to enter lengthy notes into the patient's exam record.

VI. Additional Illustrative Examples

The following numbered clauses show further illustrative examples only:

1. A method comprising:

assigning a patient to a local eyecare technician, wherein the patient and the local eyecare technician are located at a local diagnostic center;

assigning, by the local eyecare technician, the patient to a remote eyecare technician, wherein the remote eyecare technician is located at a remote diagnostic center;

collecting, by the local eyecare technician, medical history for the patient; administering, by the local eyecare technician, pre-refraction tests on the patient to produce pre-refraction results for the patient;

transmitting the medical history for the patient and the pre-refraction results for the patient to the remote eyecare technician;

administering, by the remote eyecare technician, refraction tests on the patient to produce refraction results for the patient; and transmitting to an eyecare doctor the medical history for the patient, the pre-refraction results for the patient and the refraction results for the patient.

2. The method as in claim 1, wherein the eyecare doctor, the remote technician and the local technicians are in different locations.

3. The method as in claim 2, wherein the process of administering, by the remote eyecare technician, refraction tests on the patient to produce refraction results for the patient involves the use of a remotely-controlled phoropter and videoconferencing.

4. The method as in claim 3 wherein the refraction tests comprise a normal visual acuity test and a subjective distance vision refraction test.

5. The method as in claim 4, wherein the refraction tests further comprises a subjective near vision refraction test.

6. The method as in claim 2, further comprising:
reviewing, by the eyecare doctor, the medical history for the patient, the pre-refraction results for the patient and the refraction results for the patient.

7. The method as in claim 6, wherein the process of reviewing, by the eyecare doctor, the medical history for the patient, the pre-refraction results for the patient and the refraction results for the patient involves the use of a remotely-controlled phoropter and videoconferencing by the eyecare doctor.

8. The method as in claim 7 wherein if the process of reviewing, by the eyecare doctor, the medical history for the patient, the pre-refraction results for the patient and the refraction results for the patient by the eyecare doctor involves contact lenses, instructing the local eyecare technician and the patient to try on trial contact lenses.

9. The method as in claim 8, further comprising:
collecting, by the local eyecare technician, slit lamp images from the patient with the trial contact lenses in place; and transmitting the slit lamp images to the eyecare doctor.

10. The method as in claim 7, further comprising:
issuing, by the eyecare doctor, an eye-related prescription for the patient.

11. The method as in claim 10, further comprising:
printing the eye-related prescription for the patient at the local diagnostic center.

12. A system for providing eye health and vision examinations, comprising: a diagnostic center including ophthalmic equipment comprising a set of instruments that are utilized in administering eye examinations and being coupled to an equipment controller that is configured to receive instructions for controlling the ophthalmic equipment, wherein the diagnostic center is configured to:
in response to receiving a first request from the diagnostic center, select a subset of remote technicians to administer an eye examination based, at least in part, on analyzing availability data to identify at least one remote technician who is logged into the web-based platform and not currently providing real-time eye examinations;
transmit a second request over a network to a select remote technician to administer the eye examination in real-time for a patient located at the diagnostic center;
receive first instructions over the network to permit the select remote technician to control operation of the ophthalmic equipment at the diagnostic center from a first remote location in order to administer at least one test pertaining to the eye examination;
generate patient examination data pertaining to the at least one test administered using the ophthalmic equipment;
in response to receiving a third request from the diagnostic center, select a subset of eyecare doctors to review the eye examinations based, at least in part, on analyzing the availability data to identify at least one eyecare doctor who is logged into the web-based platform and not currently providing real-time eye examinations;
transmit a fourth request over the network to a select eyecare doctor to review the eye examination in real-time for the patient located at the diagnostic center;
receive second instructions over the network to permit the select eyecare doctor to control operation of the ophthalmic equipment at the diagnostic center from a second remote location in order to review the at least one test pertaining to the eye examination; and
review the patient examination data pertaining to the at least one test administered using the ophthalmic equipment;
wherein the eyecare doctor, the remote technician and the patient are in different locations.

13. The system as in claim 12, wherein the at least one test pertaining to the eye examination comprise a pinhole visual acuity test, a normal visual acuity test, and a subjective distance vision refraction test.

14. The system as in claim 13, wherein the at least one test pertaining to the eye examination further comprises a subjective near vision refraction test.

15. The system as in claim 12 wherein the diagnostic center is further configured to: if the patient examination data includes data related to contact lenses, instruct the patient to try on trial contact lenses.

16. The system as in claim 15, wherein the diagnostic center is further configured to: obtain slit lamp images from the patient with the trial contact lenses in place and transmit the slit lamp images to the eyecare doctor.

17. The system as in claim 12, wherein the diagnostic center is further configured to: transmit an eye-related prescription from the eyecare doctor for the patient.

18. The system as in claim 17, wherein the diagnostic center is further configured to: print the eye-related prescription for the patient at the diagnostic center.

19. The system as in claim 12, wherein the diagnostic center is further configured to: administer access to the network for the patient, the remote technician and the eyecare doctor.

20. The system as in claim 19, wherein the diagnostic center is further configured to: store the patient examination data in an electronic medical records-based protocol.

VII. Conclusion

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having,"

"includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A system for facilitating comprehensive eye examinations, comprising:
a diagnostic center including:
ophthalmic equipment configured for use in an eye examination of a patient located at the diagnostic center,
an equipment controller configured to receive instructions for controlling operation of the ophthalmic equipment from multiple remote locations during the eye examination, and
a computing system coupled to the ophthalmic equipment; and
a server system configured to perform operations comprising:
receiving, over a network and from the diagnostic center, patient data that pertains to the eye examination;
selecting, based on the received patient data, a remote technician to administer the eye examination from a first remote location, wherein:
the remote technician is selected from among a set of remote technicians that are associated with a web-based platform, and
the selection of the remote technician is based at least on analyzing availability data of the set of remote technicians to identify a remote technician that is logged into the web-based platform;
assigning a first connection through which communications are facilitated with a computing device of the remote technician;
transmitting, based on the first connection assigned to the computing device of the remote technician and over the network and to the computing device of the remote technician, data indicating (i) the patient data, and (ii) permission being granted to the remote technician to administer the eye examination from the first remote location by controlling the equipment controller to operate the ophthalmic equipment during the eye examination;
generating, based on input data received from the computing device of the remote technician, examination data representing results of one or more tests administered by the remote technician during a first portion of the eye examination;
selecting a remote eyecare doctor to evaluate the examination data from a second remote location that is remote from the first remote location, wherein:
the remote eyecare doctor is selected from among a set of remote eyecare doctors that are associated with the web-based platform, and
the selection of the remote eyecare doctor is based at least on analyzing availability data of the set of remote eyecare doctors to identify a remote eyecare doctor that is logged into the web-based platform;
assigning a second connection through which communications are facilitated with a computing device of the remote eyecare doctor;
transmitting, based on the second connection assigned to the computing device of the remote eyecare doctor and over the network and to the computing device of the remote eyecare doctor, data indicating (i) the patient data, (ii) the examination data, and (iii) permission being granted to the remote eyecare doctor to:
evaluate the examination data transmitted to the second remote location, and
further administer the eye examination from the second remote location by controlling the equipment controller to operate the ophthalmic equipment during a second portion of the eye examination, and
receiving, over the network and from the computing device of the remote eyecare doctor, evaluation data representing an evaluation, by the remote eyecare doctor, of results from the one or more tests during the first portion of the eye examination; and
transmitting, over the network, the evaluation data to the computing system coupled to the ophthalmic equipment.

2. The system of claim 1, wherein:
the diagnostic center is located in a first geographic location;
the first remote location is located in a second geographic location;
the second remote location is located in a third geographic location; and
the first geographic location, the second geographic location, and the third geographic location are each different geographic locations.

3. The system of claim 1, wherein:
the patient data comprises (i) medical history information of the patient, and (ii) result data of a pre-refraction test performed on the patient at the diagnostic center by a local technician located at the diagnostic center; and the server system is configured to select the remote technician to administer the eye examination based on the medical history information of the patient and the result data of the pre-refraction test.

4. The system of claim 1, wherein:

the ophthalmic equipment comprises a phoropter located at the diagnostic center;

the permission granted to the remote technician comprises permission being granted to the remote technician to control the phoropter from the first remote location; and the permission granted to the remote eyecare doctor comprises permission being granted to the remote eyecare doctor to control the phoropter from the second remote location.

5. The system of claim 4, wherein:

the remote eyecare doctor is granted permission to control the phoropter from the second remote location after the remote technician is granted permission to control the phoropter from the first remote location; and the remote eyecare doctor and the remote technician are each granted permission to control the phoropter during the same eye examination.

6. The system of claim 4, wherein:

the remote eyecare doctor is granted permission to control the phoropter from the second remote location after the remote technician has completed administering the one or more tests during the first portion of the eye examination; and the remote eyecare doctor and the remote technician are each granted permission to control the phoropter during the same eye examination.

7. The system of claim 1, wherein the eye examination comprises at least one of:

a pinhole visual acuity test administered by the remote technician from the first remote location;

a normal visual acuity test administered by the remote technician from the first remote location;

a subjective distance vision refraction test administered by the remote technician from the first remote location;

a subjective near vision refraction test administered by the remote technician from the first remote location; and the server system is configured to transmit data indicating permission being granted to the remote technician to administer at least one of the pinhole visual acuity test, the normal visual acuity test, and the subjective near vision refraction test.

8. The system of claim 1, wherein:

the evaluation data indicates contact lens prescription for the patient based on results of the eye examination; and the computing system coupled to the ophthalmic equipment is configured to provide an indication for the patient to try on a set of contact lenses corresponding to the contact lens prescription.

9. The system of claim 1, wherein the server system is further configured to perform operations comprising:

encrypting, based on applying a medical record protocol, the patient data, the examination data, and the evaluation data; and storing the patient data, the examination data, and the evaluation data that have been encrypted based on applying the medical record protocol.

10. The system of claim 1, wherein assigning the first connection comprises assigning a first connection port through which communications are facilitated with the computing device of the remote technician.

11. The system of claim 10, wherein assigning the second connection comprises assigning a second connection port through which communications are facilitated with the computing device of the remote eyecare doctor.

12. The system of claim 1, wherein the server system is configured to perform operations comprising:

receiving, over the network, a communication based on the first connection;

determining whether an Internet Protocol (IP) address specified in the communication matches a verified IP address corresponding to the computing device of the remote technician; and transmitting the data indicating permission being granted to the remote technician to administer the eye examination based on the determination of whether the IP address specified in the communication matches the verified IP address corresponding to the computing device of the remote technician.

13. The system of claim 12, wherein:

determining whether the IP address specified in the communication matches the verified IP address corresponding to the computing device of the remote technician comprises determining that the IP address specified in the communication matches the verified IP address corresponding to the computing device of the remote technician; and transmitting the data indicating permission being granted to the remote technician to administer the eye examination based on the determination that the IP address specified in the communication matches the verified IP address corresponding to the computing device of the remote technician.

14. The system of claim 12, wherein:

determining whether the IP address specified in the communication matches the verified IP address corresponding to the computing device of the remote technician comprises determining that the IP address specified in the communication does not match the verified IP address corresponding to the computing device of the remote technician; and terminating the first connection based on the determination that the IP address specified in the communication does not match the verified IP address corresponding to the computing device of the remote technician.

15. A method performed by one or more computing devices, the method comprising:

receiving, over a network and from a diagnostic center, patient data that pertains to an eye examination, wherein the diagnostic center includes:

ophthalmic equipment configured for use in an eye examination of a patient located at the diagnostic center, an equipment controller configured to receive instructions for controlling operation of the ophthalmic equipment from multiple remote locations during the eye examination, and a computing system coupled to the ophthalmic equipment;

selecting, based on the received patient data, a remote technician to administer the eye examination from a first remote location, wherein:

the remote technician is selected from among a set of remote technicians that are associated with a web-based platform, and the selection of the remote technician is based at least on analyzing availability data of the set of remote technicians to identify a remote technician that is logged into the web-based platform;

assigning a first connection through which communications are facilitated with a computing device of the remote technician;

transmitting, based on the first connection assigned to the computing device of the remote technician and over the network and to the computing device of the remote technician, data indicating (i) the patient data, and (ii) permission being granted to the remote technician to administer the eye examination from the first remote location by controlling the equipment controller to operate the ophthalmic equipment during the eye examination;

generating, based on input data received from the computing device of the remote technician, examination data representing results of one or more tests administered by the remote technician during a first portion of the eye examination;

selecting a remote eyecare doctor to evaluate the examination data from a second remote location that is remote from the first remote location, wherein:
the remote eyecare doctor is selected from among a set of remote eyecare doctors that are associated with the web-based platform, and
the selection of the remote eyecare doctor is based at least on analyzing availability data of the set of remote eyecare doctors to identify a remote eyecare doctor that is logged into the web-based platform;

assigning a second connection through which communications are facilitated with a computing device of the remote eyecare doctor;

transmitting, based on the second connection assigned to the computing device of the remote eyecare doctor and over the network and to the computing device of the remote eyecare doctor, data indicating (i) the patient data, (ii) the examination data, and (iii) permission being granted to the remote eyecare doctor to:
evaluate the examination data transmitted to the second remote location, and
further administer the eye examination from the second remote location by controlling the equipment controller to operate the ophthalmic equipment during a second portion of the eye examination, and receiving, over the network and from the computing device of the remote eyecare doctor, evaluation data representing an evaluation, by the remote eyecare doctor, of results from the one or more tests during the first portion of the eye examination; and transmitting, over the network, the evaluation data to the computing system coupled to the ophthalmic equipment.

16. The method of claim 15, wherein:
the diagnostic center is located in a first geographic location;
the first remote location is located in a second geographic location;
the second remote location is located in a third geographic location; and
the first geographic location, the second geographic location, and the third geographic location are each different geographic locations.

17. The method of claim 15, wherein:
the patient data comprises (i) medical history information of the patient, and (ii) result data of a pre-refraction test performed on the patient at the diagnostic center by a local technician located at the diagnostic center; and
selecting the remote technician to administer the eye examination comprises selecting the remote technician based on the medical history information of the patient and the result data of the pre-refraction test.

18. The method of claim 15, wherein:
the ophthalmic equipment comprises a phoropter located at the diagnostic center;
the permission granted to the remote technician comprises permission being granted to the remote technician to control the phoropter from the first remote location; and
the permission granted to the remote eyecare doctor comprises permission being granted to the remote eyecare doctor to control the phoropter from the second remote location.

19. A system for facilitating comprehensive eye examinations, comprising:
a diagnostic center including:
equipment means for conducting an eye examination of a patient located at the diagnostic center,
a controller means for receiving instructions for controlling operation of the equipment means from multiple remote locations during the eye examination, and
a computing means for exchanging communications with the equipment means; and
a server means for performing operations comprising:
receiving, over a network and from the diagnostic center, patient data that pertains to the eye examination;
selecting, based on the received patient data, a remote technician to administer the eye examination from a first remote location, wherein:
the remote technician is selected from among a set of remote technicians that are associated with a web-based platform, and
the selection of the remote technician is based at least on analyzing availability data of the set of remote technicians to identify a remote technician that is logged into the web-based platform;
assigning a first connection through which communications are facilitated with a computing device of the remote technician;
transmitting, based on the first connection assigned to the computing device of the remote technician and over the network and to the computing device of the remote technician, data indicating (i) the patient data, and (ii) permission being granted to the remote technician to administer the eye examination from the first remote location by controlling the controller means to operate the equipment means during the eye examination;
generating, based on input data received from the computing device of the remote technician, examination data representing results of one or more tests administered by the remote technician during a first portion of the eye examination;
selecting a remote eyecare doctor to evaluate the examination data from a second remote location that is remote from the first remote location, wherein:
the remote eyecare doctor is selected from among a set of remote eyecare doctors that are associated with the web-based platform, and
the selection of the remote eyecare doctor is based at least on analyzing availability data of the set of remote eyecare doctors to identify a remote eyecare doctor that is logged into the web-based platform;

assigning a second connection through which communications are facilitated with a computing device of the remote eyecare doctor;

transmitting, based on the second connection assigned to the computing device of the remote eyecare doctor and over the network and to the computing device of the remote eyecare doctor, data indicating (i) the patient data, (ii) the examination data, and (iii) permission being granted to the remote eyecare doctor to:
- evaluate the examination data transmitted to the second remote location, and
- further administer the eye examination from the second remote location by controlling the controller means to operate the equipment means during a second portion of the eye examination, and receiving, over the network and from the computing device of the remote eyecare doctor, evaluation data representing an evaluation, by the remote eyecare doctor, of results from the one or more tests during the first portion of the eye examination; and transmitting, over the network, the evaluation data to the computing means.

20. The system of claim 19, wherein:

the diagnostic center is located in a first geographic location;

the first remote location is located in a second geographic location;

the second remote location is located in a third geographic location; and the first geographic location, the second geographic location, and the third geographic location are each different geographic locations.

* * * * *